(12) United States Patent
Tanaka et al.

(10) Patent No.: US 7,683,186 B2
(45) Date of Patent: Mar. 23, 2010

(54) OPTICALLY ACTIVE BIARYL PHOSPHORUS COMPOUND AND PRODUCTION PROCESS THEREOF

(75) Inventors: Ken Tanaka, Fuchu (JP); Wataru Kuriyama, Hiratsuka (JP)

(73) Assignees: National University Corporation Tokyo University of Agriculture and technology, Tokyo (JP); Takasago International Corporation, Tokyo (JP)

( * ) Notice: Subject to any disclaimer, the term of this patent is extended or adjusted under 35 U.S.C. 154(b) by 122 days.

(21) Appl. No.: 12/000,083

(22) Filed: Dec. 7, 2007

(65) Prior Publication Data

US 2008/0139822 A1 Jun. 12, 2008

(30) Foreign Application Priority Data

Dec. 11, 2006 (JP) .............................. 2006-333713

(51) Int. Cl.
C07D 209/12 (2006.01)
C07D 307/87 (2006.01)
C07D 333/72 (2006.01)
C07F 9/40 (2006.01)

(52) U.S. Cl. ........................... 549/220; 548/414; 549/6; 549/8; 556/404

(58) Field of Classification Search ................... 568/17, 568/13, 8
See application file for complete search history.

(56) References Cited

U.S. PATENT DOCUMENTS

| 5,399,771 A | | 3/1995 | Cai et al. | |
| 5,530,150 A | * | 6/1996 | Takaya et al. | ................. 556/18 |
| 5,872,273 A | | 2/1999 | Saito et al. | |
| 5,922,918 A | * | 7/1999 | Zhang et al. | ................... 568/17 |

FOREIGN PATENT DOCUMENTS

| JP | 10-501234 | 2/1998 |
| JP | 10-182678 | 7/1998 |
| JP | 2000-016997 | 1/2000 |

OTHER PUBLICATIONS

Ballie, C.; Xiao, J. Tetrahedron 2004, 60, 4159-4168.*
Nishida et al. Angew Chem. Int. Ed. 2007, 46, 3951-3954.*
Kondoh et al. J. Am. Chem. Soc. 2007, 129, 6996-6997.*
H. Shimizu et al., "Recent Advances in Biaryl-Type Bisphosphine Ligands", Tetrahedron, vol. 61, pp. 5405-5432, 2005.
G. Nishida et al., "Enantioselective Synthesis of Tetra-Ortho-Substituted Axially Chiral Biaryls through Rhodium-Catalyzed Double [2 + 2 + 2] Cycloaddition", Organic Letters, vol. 8, No. 16, pp. 3489-3492, 2006.
B. Heller et al., "Phosphorus-Bearing Axially Chiral Biaryls by Catalytic Asymmetric Cross-Cyclotrimerization and a First Application in Asymmetric Hydrosilylation", Chem. Eur. J., vol. 13, No. 4, pp. 1117-1128, 2007.
G. Onodera et al., "Ruthenium-Catalyzed Formation of Aryl(diphenyl)phosphine Oxides by Reactions of Propargylic Alcohols with Diphenylphosphine Oxide", Organic Letters, vol. 7, No. 18, pp. 4029-4032, 2005.
S. Doherty et al., "Rhodium-Catalyzed Double [2+2+2] Cycloaddition of 1,4-Bis(diphenylphosphinoyl)buta-1,3-diyne with Tethered Diynes: A Modular, Highly Versatile Single-Pot Synthesis of NU-BIPHEP Biaryl Diphosphines", Organic Letters, vol. 9, No. 23, pp. 4925-4928, 2007.
A. Kondoh et al., "Synthesis of Bulky Phosphines by Rhodium-Catalyzed Formal [2+2+2] Cycloaddition Reactions of Tethered Diynes with 1-Alkynylphosphine Sulfides", J. Am. Chem. Soc., vol. 129, No. 22, pp. 6996-6997, 2007.
G. Nishida et al., "Asymmetric Assembly of Aromatic Rings to Produce Tetra-*ortho*-Substituted Axially Chiral Biaryl Phosphorus Compounds", Angew. Chem. Int. Ed., vol. 46, No. 21, pp. 3951-3954, 2007.

* cited by examiner

*Primary Examiner*—Rebecca L Anderson
*Assistant Examiner*—Matthew P Coughlin
(74) *Attorney, Agent, or Firm*—Wenderoth Lind & Ponack, L.L.P.

(57) ABSTRACT

A phosphorus compound of formula (1):

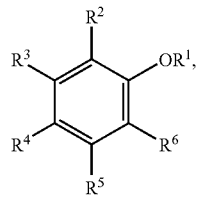

(1)

wherein $R^1$ denotes a hydrogen atom or a hydroxy protective group; $R^2$ denotes a group defined by the following formula ($R^2$-1) or ($R^2$-2); $R^3$, $R^4$, $R^5$, and $R^6$ may be the same or different and independently denote a hydrogen atom, an alkyl group, an alkoxy group, an acyloxy group, a halogen atom, a haloalkyl group, or a dialkylamino group; two among $R^3$, $R^4$, $R^5$, and $R^6$ may form an aromatic ring optionally having a substituent group, and two among $R^3$, $R^4$, $R^5$, and $R^6$ may form a methylene chain optionally having a substituent group or a (poly)methylenedioxy group optionally having a substituent group:

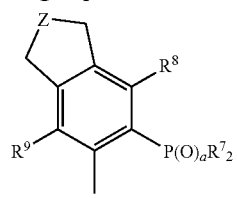

($R^2$-1)

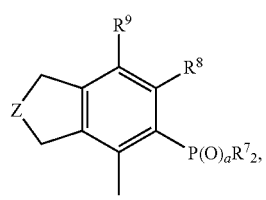

($R^2$-2)

wherein ($R^2$-1) and ($R^2$-2), $R^7$ denotes an alkyl group, a cycloalkyl group, an aryl group, an alkoxy group, or an aryloxy group; $R^8$ and $R^9$ independently denote a hydrogen atom, an alkyl group, or an aryl group; z denotes a divalent group; and a denotes an integer of 0 or 1.

11 Claims, No Drawings

OPTICALLY ACTIVE BIARYL PHOSPHORUS COMPOUND AND PRODUCTION PROCESS THEREOF

BACKGROUND OF THE INVENTION (1) Field of the Invention

The invention relates to a phosphorus compound useful as a ligand of a metal catalyst and a production process thereof.

(2) Description of the Related Art

Conventionally, many reports have been published on transition metal complexes usable as a catalyst for an asymmetric reaction such as asymmetric hydrogenation reaction, asymmetric isomerization reaction, and asymmetric hydrosilylation reaction. Especially, complexes containing a transition metal such as ruthenium, rhodium, iridium, palladium, or the like and an optically active phosphine compound coordinated with the metal have widely been known as a high performance catalyst for an asymmetric synthesis reaction. Among such optically active phosphine compounds, an optically active biaryl phosphine compound with axial asymmetry is useful as an optically active ligand of an asymmetric reaction catalyst (see, for example, Tetrahedron, 2005, Vol. 61, 5405-5432). Many of the processes to synthesize such an optically active biaryl compound involve homo- or cross-coupling of two aryl units, and require optical resolution to obtain an optically active substance after the coupling (see, for example, JP-A-2000-16997 and JP-A-10-182678). To synthesize an optically active biaryl phosphine compound, it is required to introduce a phosphorus atom site into the biaryl skeleton before or after the synthesis of the biaryl compound by the above-mentioned homo- or cross-coupling (see, for example, JP-A-10-182678 and JP-T-10-501234). On the other hand, recently, as a new technique for synthesizing an optically active biaryl compound, a technique involving enantio-selective [2+2+2] cycloaddition reaction using alkynes has also been developed (Organic Letters, 2006, Vol. 8, 3489-3492).

SUMMARY OF THE INVENTION

As described above, although the synthesis of a biaryl compound having an axially asymmetric structure by way of enantio-selective [2+2+2] cycloaddition reaction has been known, no process for synthesizing a compound with a phosphorus atom site introduced into the biaryl skeleton thereof is hitherto known.

Furthermore, it is indispensable to carry out optical resolution for a biaryl phosphorus compound synthesized by a conventional coupling method of aryl units and in some cases, one optical isomer may be unnecessary.

Therefore, if it is possible to produce optically active biaryl phosphorus compound having high optical purity and axially asymmetric structure using a substrate relatively easy to obtain through a lessened number of steps, an axially asymmetric optically active substance can easily be obtained without the step of optical resolution, which is almost indispensable step in a conventional method. The purpose of the invention is to provide such a production process and a novel biaryl phosphorus compound to be produced in such a manner.

As a result of keen examination to solve the problems, the inventors have found that it is possible to produce an axially asymmetric biaryl phosphorus compound having high optical purity in one step by enantio-selective [2+2+2] cycloaddition reaction of a diyne compound and an alkynyl phosphorus compound in the presence of a catalyst containing rhodium and an optically active bisphosphine, and have completed the present invention.

The invention includes:

1. A phosphorus compound defined by the following general formula (1):

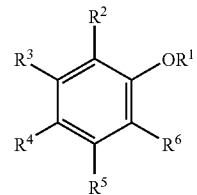

(1)

in the formula (1), $R^1$ denotes a hydrogen atom or a hydroxy protective group; $R^2$ denotes a group defined by the following formula ($R^2$-1) or ($R^2$-2); $R^3$, $R^4$, $R^5$, and $R^6$ may be the same or different and independently denote a hydrogen atom, an alkyl group, an alkoxy group, an acyloxy group, a halogen atom, a haloalkyl group, or a dialkylamino group; two among $R^3$, $R^4$, $R^5$, and $R^6$ may form an aromatic ring optionally having a substituent group, and two among $R^3$, $R^4$, $R^5$, and $R^6$ may form a methylene chain optionally having a substituent group or a (poly)methylenedioxy group optionally having a substituent group:

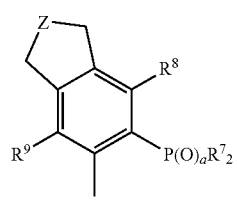

($R^2$-1)

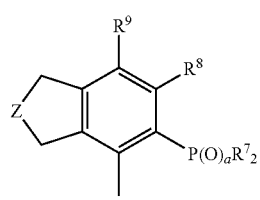

($R^2$-2)

in the formula ($R^2$-1) and ($R^2$-2), $R^7$ denotes an alkyl group, a cycloalkyl group, an aryl group, an alkoxy group, or an aryloxy group; $R^8$ and $R^9$ independently denote a hydrogen atom, an alkyl group, or an aryl group; z denotes a divalent group; and a denotes an integer of 0 or 1.

2. The phosphorus compound according to the above-mentioned 1, being an axially asymmetric optically active substance.

3. The phosphorus compound according to the above-mentioned 1, defined by the following general formula (3):

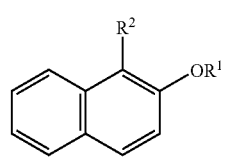

(3)

in the formula (3), $R^1$ denotes a hydrogen atom or a hydroxy protective group; $R^2$ denotes a group defined by the following formula ($R^2$-1) or ($R^2$-2):

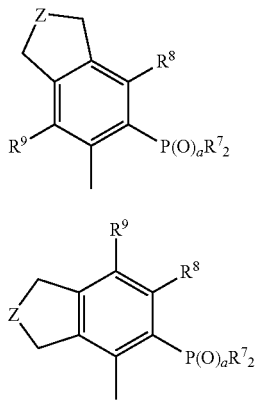

(R²-1)

(R²-2)

in the formula ($R^2$-1) and ($R^2$-2), $R^7$ denotes an alkyl group, a cycloalkyl group, an aryl group, an alkoxy group, or an aryloxy group; $R^8$ and $R^9$ independently denote a hydrogen atom, an alkyl group, or an aryl group; z denotes a divalent group; and a denotes an integer of 0 or 1.

4. The phosphorus compound according to the above-mentioned 3, being an axially asymmetric optically active substance.

5. A production process of the phosphorus compound according to the above-mentioned 2, wherein a diyne compound defined by the following general formula (2-1) and an alkynyl phosphorus compound defined by the following general formula (3-1) are reacted using a catalyst containing rhodium metal and an optically active bisphosphine:

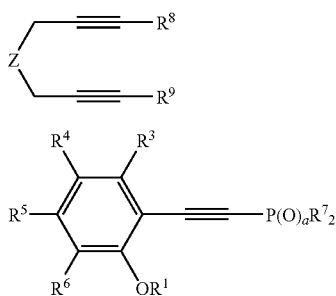

(2-1)

(3-1)

in the formula (2-1), $R^8$ and $R^9$ independently denote a hydrogen atom, an alkyl group, or an aryl group; z denotes a divalent group: and in the formula (3-1), $R^1$ denotes a hydrogen atom or a hydroxy protective group; $R^3$, $R^4$, $R^5$, and $R^6$ may be the same or different and independently denote a hydrogen atom, an alkyl group, an alkoxy group, an acyloxy group, a halogen atom, a haloalkyl group, or a dialkylamino group; two among $R^3$, $R^4$, $R^5$, and $R^6$ may form an aromatic ring optionally having a substituent group, and two among $R^3$, $R^4$, $R^5$, and $R^6$ may form a methylene chain optionally having a substituent group or a (poly)methylenedioxy group optionally having a substituent group; $R^7$ denotes an alkyl group, a cycloalkyl group, an aryl group, an alkoxy group, or an aryloxy group; and a denotes an integer of 0 or 1.

6. A production process of the phosphorus compound according to the above-mentioned 2, wherein a diyne compound defined by the following general formula (2-2) and an alkynyl phosphorus compound defined by the following general formula (3-2) are reacted using a catalyst containing rhodium metal and an optically active bisphosphine:

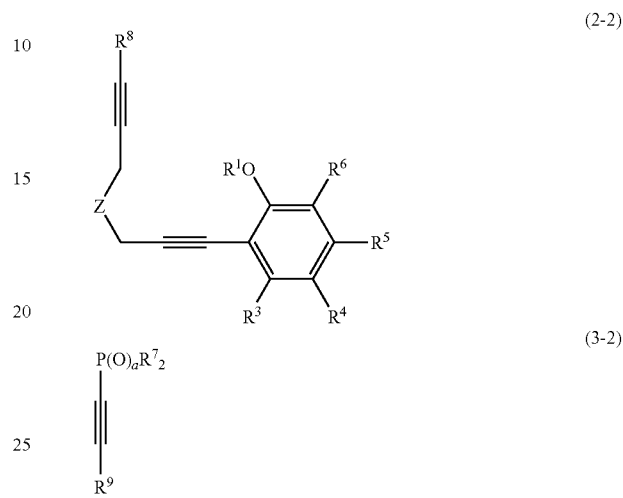

(2-2)

(3-2)

in the formula (2-2), $R^1$ denotes a hydrogen atom or a hydroxy protective group; $R^3$, $R^4$, $R^5$, and $R^6$ may be the same or different and independently denote a hydrogen atom, an alkyl group, an alkoxy group, an acyloxy group, a halogen atom, a haloalkyl group, or a dialkylamino group; two among $R^3$, $R^4$, $R^5$, and $R^6$ may form an aromatic ring optionally having a substituent group, and two among $R^3$, $R^4$, $R^5$, and $R^6$ may form a methylene chain optionally having a substituent group or a (poly)methylenedioxy group optionally having a substituent group; $R^8$ denotes a hydrogen atom, an alkyl group, or an aryl group; z denotes a divalent group: and in the formula (3-2), $R^7$ denotes an alkyl group, a cycloalkyl group, an aryl group, an alkoxy group, or an aryloxy group; $R^9$ denotes a hydrogen atom, an alkyl group, or an aryl group; and a denotes an integer of 0 or 1.

7. The production process according to the above-mentioned 5 or 6, wherein the catalyst containing rhodium metal and an optically active bisphosphine is a compound defined by the following general formula (4):

$$[Rh(L)_m(Y)_n]X \quad (4)$$

in the formula (4), L denotes an optically active bisphosphine defined by the following formula (5); Y denotes a nonconjugated diene compound; X denotes a counter anion; m denotes an integer of 1 or 2; n denotes an integer of 0 or 1; however, in the case where m=1, n=0 or n=1; and in the case where m=2, n=0:

$$R^{10}R^{11}P\text{-}Q\text{-}PR^{12}R^{13} \quad (5)$$

in the formula (5), $R^{10}$, $R^{11}$, $R^{12}$, and $R^{13}$ independently denote an aryl group optionally having a substituent group or a cycloalkyl group optionally having a substituent group; $R^{10}$ in combination with $R^{11}$ and/or $R^{12}$ in combination with $R^{13}$ may form a ring; and Q denotes a divalent arylene group optionally having a substituent group or a ferrocenediyl group.

8. The production process according to the above-mentioned 7, wherein the catalyst containing rhodium metal and an optically active bisphosphine is used immediately after preparation.
9. The production process according to the above-mentioned 7 or 8, wherein an olefin ligand is eliminated using hydrogen gas in preparing the catalyst containing rhodium metal and an optically active bisphosphine.
10. An asymmetric synthesis reaction using the axially asymmetric optically active compound according to the above-mentioned 2 or 4.

According to the process of the invention, since it is possible to enantio-selectively produce an optically active biaryl phosphorus compound in one step by reacting a diyne compound and an alkynyl phosphorus compound in the presence of a catalyst containing rhodium metal and an optically active bisphosphine, an optically active biaryl phosphorus compound can be produced easily using a substrate relatively easy to obtain and consequently, an axially asymmetric and optically active substance can be obtained without the step of optical resolution. Furthermore, a phosphorus compound within the scope of the invention can easily be produced and is useful as a ligand of a metal catalyst.

DETAILED DESCRIPTION OF THE INVENTION

Hereinafter, the invention will be described in more detail.

A phosphorus compound of the invention is a phosphorus compound defined by the above-mentioned general formula (1) and can be produced by a production process of the invention, which will be described in detail below. In the general formula (1), $R^1$ denotes a hydrogen atom or a hydroxy protective group and examples of the hydroxy protective group defined by $R^1$ may include an alkyl, an aralkyl, an acyl, or a tri-substituted silyl group.

Herein, the alkyl group defined by $R^1$ may include, for example, linear or branched alkyl groups having 1 to 15 carbon atoms, preferably 1 to 10 carbon atoms, and more preferably 1 to 6 carbon atoms. Specific examples are methyl, ethyl, n-propyl, isopropyl, n-butyl, sec-butyl, isobutyl, tert-butyl, pentyl, and hexyl group. These alkyl groups may have an alkoxy substituent group, and specific examples of the alkoxyalkyl may include methoxymethyl, ethoxyethyl, tert-butoxymethyl, and 2-methoxyethoxyethyl.

The aralkyl group defined by $R^1$ may include, for example, benzyl, p-methoxybenzyl, 1-phenylethyl, and triphenylmethyl group.

The acyl group defined by $R^1$ may include, for example, linear or branched aliphatic acyl groups having 1 to 10 carbon atoms or aromatic acyl groups. Specific examples may include acetyl, propanoyl, butyryl, pivaloyl, methoxycarbonyl, ethoxycarbonyl, benzyloxycarbonyl, benzoyl, and p-nitrobenzoyl group.

The tri-substituted silyl group defined by $R^1$ may include, for example, trimethylsilyl, triethylsilyl, triisopropylsilyl, and tert-butyldimethylsilyl group.

In the general formula (1), $R^2$ denotes a group defined by the above-mentioned formula ($R^2$-1) or ($R^2$-2), and in the formulas ($R^2$-1) and ($R^2$-2), $R^7$ denotes an alkyl, a cycloalkyl, an aryl, an alkoxy, or an aryloxy group.

Herein, the alkyl group defined by $R^7$ may include, for example, linear or branched alkyl groups having 1 to 15 carbon atoms, preferably 1 to 10 carbon atoms, and more preferably 1 to 6 carbon atoms. Specific examples are methyl, ethyl, n-propyl, isopropyl, n-butyl, sec-butyl, isobutyl, tert-butyl, pentyl, and hexyl group.

The cycloalkyl group defined by $R^7$ may include, for example, cycloalkyl groups having 3 to 8 carbon atoms, and specific examples are cyclopropyl, cyclobutyl, cyclopentyl, cyclohexyl, cycloheptyl, and cyclooctyl group.

The aryl group defined by $R^7$ may include, for example, aryl groups having 6 to 18 carbon atoms, and specific examples are phenyl, naphthyl, anthryl, phenanthryl, and biphenyl group. These aryl groups may have a substituent group and examples of the substituent group may be linear or branched alkyl groups having 1 to 6 carbon atoms such as methyl and tert-butyl; linear or branched alkoxy groups having 1 to 6 carbon atoms such as methoxy and tert-butoxy; and halogen atoms such as chlorine, bromine, and fluorine; and a plurality of these substituent groups may be introduced into the aryl groups. Specific examples of these aryl groups having substituent groups are p-tolyl, m-tolyl, o-tolyl, 3,5-xylyl, 3,5-di-tert-butylphenyl, p-tert-butylphenyl, p-methoxyphenyl, 3,5-di-tertbutyl-4-methoxyphenyl, p-chlorophenyl, and m-fluorophenyl group.

The alkoxy group defined by $R^7$ may include, for example, linear or branched alkoxy groups having 1 to 15 carbon atoms, preferably 1 to 10 carbon atoms, and more preferably 1 to 6 carbon atoms. Specific examples are methoxy, ethoxy, n-propoxy, isopropoxy, n-butoxy, sec-butoxy, isobutoxy, tert-butoxy, pentyloxy, and hexyloxy group.

The aryloxy group defined by $R^7$ may include, for example, aryloxy groups having 6 to 18 carbon atoms, and specific examples are phenyloxy, naphthyloxy, anthryloxy, phenanthryloxy, and biphenyloxy. These aryloxy groups may have a substituent group and examples of the substituent group are linear or branched alkyl groups having 1 to 6 carbon atoms such as methyl and tert-butyl; linear or branched alkoxy groups having 1 to 6 carbon atoms such as methoxy and tert-butoxy; and halogen atoms such as chlorine, bromine, and fluorine, and a plurality of these substituent groups may be introduced into the aryl group.

In the general formula (1), $R^3$, $R^4$, $R^5$, and $R^6$ may be the same or different and independently denote a hydrogen atom, an alkyl, an alkoxy, an acyloxy, a halogen atom, a haloalkyl, or a dialkylamino group.

Herein, the alkyl group defined by $R^3$, $R^4$, $R^5$, and $R^6$ may include, for example, linear or branched alkyl groups having 1 to 6 carbon atoms such as methyl and tert-butyl group; the alkoxy group may include, for example, linear or branched alkoxy groups having 1 to 6 carbon atoms such as methoxy and tert-butoxy group; the acyloxy group may include, for example, acyloxy groups having 2 to 10 carbon atoms such as acetoxy, propanoyloxy, trifluoroacetoxy, and benzoyloxy group; the halogen atom may include, for example, chlorine, bromine, and fluorine; the haloalkyl group may include, for example, haloalkyl groups having 1 to 4 carbon atoms such as trifluoromethyl group; and dialylamino group may include, for example, dimethylamino and the diethylamino group.

In the general formula (1), two among $R^3$, $R^4$, $R^5$, and $R^6$ may form an aromatic ring optionally having a substituent group and in such a case, specific examples of the aromatic ring may be a benzene ring, a naphthyl ring, an anthryl ring, and a phenanthryl ring. The substituent group of the aromatic ring may be alkyl groups and halogen atoms, and specific examples may be the above-mentioned alkyl groups having 1 to 6 carbon atoms and a fluorine atom.

Furthermore, in the general formula (1), two among $R^3$, $R^4$, $R^5$, and $R^6$ may form a methylene chain optionally having a substituent group, and in such a case, the methylene chain may be preferably methylene chains having 3 to 5 carbon atoms, and specific examples are trimethylene, tetramethylene, and pentamethylene group. The substituent group of the methylene chain may include alkyl groups and halogen atoms, and specific examples may be the above-mentioned alkyl groups having 1 to 6 carbon atoms and a fluorine atom.

Furthermore, in the general formula (1), two among $R^3$, $R^4$, $R^5$, and $R^6$ may form a (poly)methylenedioxy group optionally having a substituent group and in such a case, specific examples of the (poly)methylenedioxy may be methylenedioxy, ethylenedioxy, and trimethylenedioxy group. The substituent group of the (poly)methylenedioxy may include alkyl groups and halogen atoms, and specific examples may be the above-mentioned alkyl groups having 1 to 6 carbon atoms and a fluorine atom.

In the general formula (1), $R^2$ denotes a group defined by the above-mentioned formula ($R^2$-1) or ($R^2$-2), and in the general formulas ($R^2$-1) and ($R^2$-2), $R^8$ and $R^9$ independently denote a hydrogen atom, an alkyl, or an aryl group, and the alkyl group denoted by $R^8$ and $R^9$ may include, for example, linear or branched alkyl groups having 1 to 15 carbon atoms, preferably 1 to 10 carbon atoms, and more preferably 1 to 6 carbon atoms. Specific examples are methyl, ethyl, n-propyl, isopropyl, n-butyl, sec-butyl, isobutyl, tert-butyl, pentyl, and hexyl group.

The aryl group denoted by $R^8$ and $R^9$ may include, for example, aryl groups having 6 to 18 carbon atoms, and specific examples are phenyl, naphthyl, anthryl, phenanthryl, and biphenyl group. These aryl groups may have a substituent group, and the substituent group may include, for example, linear or branched alkyl groups having 1 to 6 carbon atoms such as methyl, ethyl, n-propyl, isopropyl, n-butyl, sec-butyl, isobutyl, tert-butyl, pentyl, and hexyl group; linear or branched alkoxy groups having 1 to 6 carbon atoms such as methoxy, ethoxy, n-propoxy, isopropoxy, n-butoxy, sec-butoxy, isobutoxy, tert-butoxy, pentyloxy, and hexyloxy group; and halogen atoms such as chlorine, bromine, and fluorine, and a plurality of these substituent groups may exist in the aryl group.

The divalent group denoted by Z in the formulas ($R^2$-1) and ($R^2$-2) may include, for example, an oxygen atom, a sulfur atom, a methylene chain, $NR^N$, and $Si(R^{Si})_2$. Herein, $R^N$ denotes an alkyl, an aryl, an alkanesulfonyl, an arylsulfonyl, or an acyl group, and $R^{Si}$ denotes an alkyl or an aryl group or may form a ring with $Si(R^{Si})_2$.

The methylene chain denoted by Z may include, for example, linear or branched methylene chains and examples are methylene, ethylene, trimethylene, propylene, isopropylidene, 2,3-butanediyl, and difluoromethylene group.

The alkyl group denoted by $R^N$ of $NR^N$ and $R^{Si}$ of $Si(R^{Si})_2$ may include, for example, linear or branched alkyl groups having 1 to 6 carbon atoms, and specific examples are the above-mentioned alkyl groups. The aryl group defined by $R^N$ and $R^{Si}$ may include the aryl groups having 6 to 18 carbon atoms, and specific examples are the above-mentioned aryl groups.

The alkanesulfonyl and arylsulfonyl group defined by $R^N$ of $NR^N$ may include, for example, methanesulfonyl, trifluoromethanesulfonyl, benzenesulfonyl, and p-toluenesulfonyl group.

The acyl group defined by $R^N$ may include, for example, linear or branched aliphatic acyl groups having 2 to 10 carbon atoms or aromatic acyl groups, and specific examples may include acetyl, propanoyl, butyryl, pivaloyl, methoxycarbonyl, ethoxycarbonyl, tert-butoxycarbonyl, benzyloxycarbonyl, benzoyl, and p-nitrobenzoyl group.

The ring formed with $Si(R^{Si})_2$ may be a silolane ring, a silane ring, or a silepane ring.

In the invention, the phosphorus compounds defined by the general formula (1) are preferably the phosphorus compounds defined by the general formula (3). The definitions of the reference characters in the general formula (3) and the examples of the groups denoted by the reference characters are the same as those described for the general formula (1). Preferable specific examples of the phosphorus compounds defined by the general formula (1) may be optically active biarylphosphine oxides or biarylphosphines exemplified in Examples described below.

Furthermore, in the invention, the phosphorus compounds defined by the general formula (1) and preferably by the general formula (3) are preferably axially asymmetric optically active compounds.

Next, a production process of an axially asymmetric optically active phosphorus compound that is suitable for producing the phosphorus compound of the invention (referred to simply as a production process of the invention in some cases) will be described.

The production process of an axially asymmetric optically active phosphorus compound of the invention involves, as described in the following schemes, causing reaction of a diyne compound defined by the general formula (2-1) with an alkynyl phosphorus compound defined by the general formula (3-1) or reaction of a diyne compound defined by the general formula (2-2) with an alkynyl phosphorus compound defined by the general formula (3-2) in the presence of a catalyst containing rhodium metal and an optically active bisphosphine compound and more particularly causing enantio-selective [2+2+2] cycloaddition.

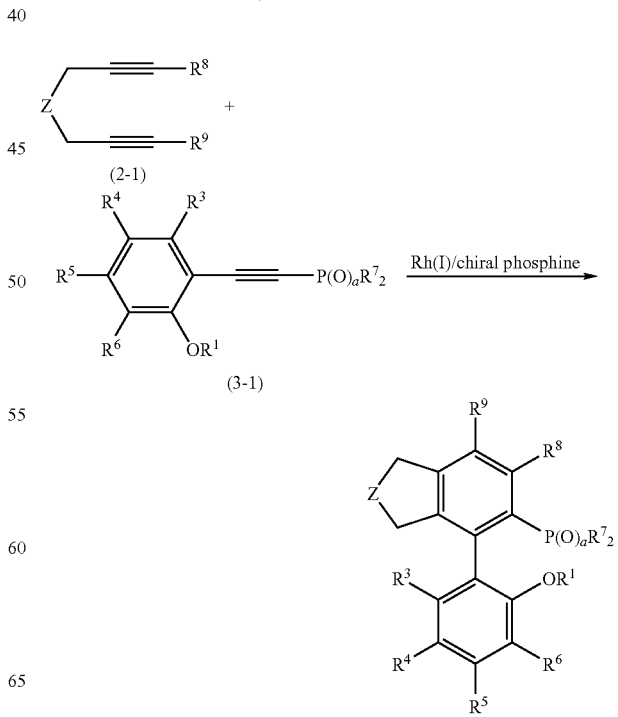

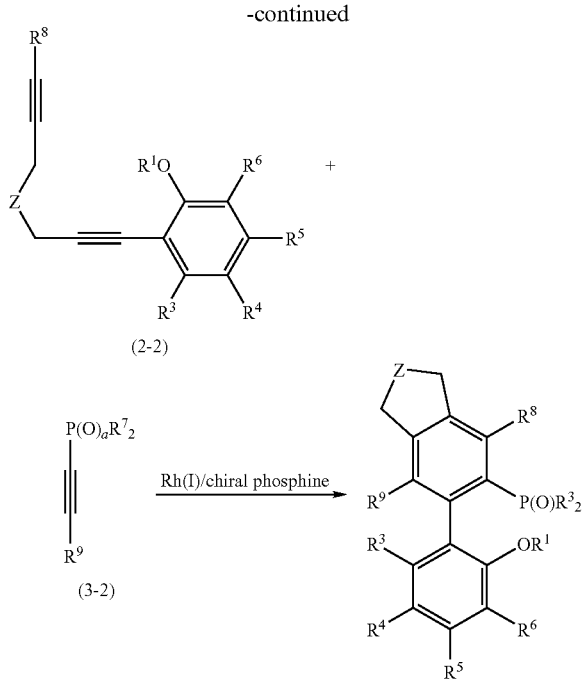

Definitions of the reference characters $R^1$, $R^2$, $R^3$, $R^4$, $R^5$, $R^6$, $R^7$, $R^8$, $R^9$, Z, and a and examples of the groups represented by these reference characters in the general formulas (2-1), (2-2), (3-1), and (3-2) described also in the schemes are the same as those described above for the general formula (1).

The catalyst containing rhodium metal and an optically active bisphosphine compound used in the production process of the invention will be described.

As the rhodium source for the rhodium metal used as one component of the catalyst of the invention, rhodium compounds may be used, and preferable rhodium compounds may be complexes of rhodium(I) having olefinic ligand. Specific examples of rhodium(I) complexes are $[Rh(cod)_2]X$, $[Rh(nbd)_2]X$, $[RhCl(ethylene)_2]_2$, $[RhCl(cod)]_2$, and $[RhCl(nbd)]_2$. In the above-mentioned chemical formulas of the complexes, X denotes a counter anion; cod denotes 1,5-cyclooctadiene; and nbd denotes norbornadiene.

Examples of the optically active bisphosphine compound that is the other catalytic component used for the invention are those defined by the following general formula (5):

$$R^{10}R^{11}P\text{-}Q\text{-}PR^{12}R^{13} \quad (5)$$

in the formula, $R^{10}$, $R^{11}$, $R^{12}$, and $R^{13}$ independently denote an aryl group optionally having a substituent group or a cycloalkyl group optionally having a substituent group; $R^{10}$ in combination with $R^{11}$ and/or $R^{12}$ in combination with $R^{13}$ may form a ring; and Q denotes a divalent arylene group optionally having a substituent group or a ferrocenediyl group.

In the above formula, the aryl group denoted by $R^{10}$, $R^{11}$, $R^{12}$, or $R^{13}$ optionally having a substituent group may be an aryl group having 6 to 14 carbon atoms, and specific examples are phenyl, naphthyl, anthryl, phenanthryl, and biphenyl group. These aryl groups may have a substituent group, and the substituent group may be an alkyl, an alkoxy, an aryl, and a heterocyclic group.

The alkyl group as a substituent group of the aryl groups may include, for example, linear or branched alkyl groups having 1 to 15 carbon atoms, preferably 1 to 10 carbon atoms, and more preferably 1 to 6 carbon atoms, and specific examples are methyl, ethyl, n-propyl, isopropyl, n-butyl, sec-butyl, isobutyl, and tert-butyl group.

The alkoxy group as a substituent group of the aryl groups may include, for example, linear or branched alkoxy groups having 1 to 6 carbon atoms, and specific examples are methoxy, ethoxy, n-propoxy, isopropoxy, n-butoxy, sec-butoxy, isobutoxy, and tert-butoxy group.

The aryl group as a substituent group of the aryl groups may include, for example, aryl groups having 6 to 14 carbon atoms, and specific examples are phenyl, naphthyl, anthryl, phenanthryl, and biphenyl group.

The heterocyclic group as the substituent group of the aryl groups may include, for example, aliphatic heterocyclic groups and aromatic heterocyclic groups. The aliphatic heterocyclic groups may include, for example, 5- to 8-membered and preferably 5- or 6-membered mono-cyclic, polycyclic, and condensed ring type aliphatic heterocyclic groups having 2 to 14 carbon atoms and at least one, preferably 1 to 3 hetero atoms such as nitrogen, oxygen, and sulfur atoms. Specific examples of the aliphatic heterocyclic groups are 2-oxo pyrrolidyl, piperidino, piperadinyl, morpholino, tetrahydrofuryl, tetrahydropyranyl, and tetrahydrothienyl. On the other hand, the aromatic heterocyclic groups may include, for example, 5- to 8-membered and preferably 5- or 6-membered monocyclic, polycyclic, and condensed ring type heteroaryl groups having 2 to 15 carbon atoms and at least one, preferably 1 to 3 hetero atoms such as nitrogen, oxygen, and sulfur atoms. Specific examples are furyl, thienyl, pyridyl, pyrimidinyl, pyradinyl, pyridadinyl, pyrazolyl, imidazolyl, oxazolyl, thiazolyl, benzofuryl, benzothienyl, quinolyl, isoquinolyl, quinoxalyl, phthalazinyl, quinazolinyl, naphthyldinyl, cinnolinyl, benzoimidazolyl, benzoxazolyl, and benzothiazolyl group.

The cycloalkyl denoted by $R^{10}$, $R^{11}$, $R^{12}$, and $R^{13}$ optionally having a substituent group may be 5- or 6-membered cycloalkyl groups, and preferable cycloalkyl groups are cyclopentyl and cyclohexyl group. These cycloalkyl groups may have one or more alkyl or alkoxy substituent groups as exemplified above for the aryl groups.

Furthermore, the ring formed by combination of $R^{10}$ with $R^{11}$ and/or $R^{12}$ with $R^{13}$ may be 4-, 5-, or 6-membered rings containing a phosphorus atom to which $R^{10}$, $R^{11}$, $R^{12}$, and $R^{13}$ are bound. Specific examples of the ring are phosphetane ring, phospholane ring, phosphane ring, 2,4-dimethylphosphetane ring, 2,4-diethylphosphetane ring, 2,5-dimethylphospholane ring, 2,5-diethylphospholane ring, 2,6-dimethylphosphane ring, and 2,6-diethylphosphane ring. These rings may be optically active substance.

The divalent arylene denoted by Q optionally having a substituent group may be phenylene, biphenyldiyl, and binaphthalenediyl group. The phenylene group includes, for example, o- or m-phenylene group, and may have substituent groups selected from alkyl group such as methyl, ethyl, n-propyl, isopropyl, n-butyl, sec-butyl, isobutyl, and tert-butyl group; alkoxy group such as methoxy, ethoxy, n-propoxy, isopropoxy, n-butoxy, sec-butoxy, isobutoxy, and tert-butoxy group; hydroxyl group; amino group; and substituted amino group. The biphenyldiyl group and the binaphthalenediyl group are preferably have a 1,1'-biaryl-2,2'-diyl type structure, and may have substituent group selected from the above-mentioned alkyl group and alkoxy group; alkylenedioxy group such as methylenedioxy, ethylenedioxy, and trimethylenedioxy; hydroxyl group; amino group; and substituted amino group. Furthermore, the ferrocenediyl group also may have substituent groups, and the substituent groups may be, for example, the above-mentioned alkyl group, alkoxy group, alkylenedioxy groups, hydroxyl group, amino group, and substituted amino group.

Specific examples of the optically active bisphosphine compound defined by the general formula (5) may be conventionally known bisphosphines, and one example is a compound defined by the following general formula (6).

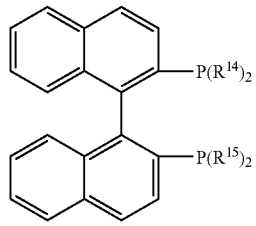

(6)

In the formula, $R^{14}$ and $R^{15}$ independently denote phenyl group optionally having a substituent group selected from a halogen atom, an alkyl group, and an alkoxy group, or denote cyclopentyl group or cyclohexyl group.

In the above $R^{14}$ and $R^{15}$, the alkyl group as the substituent group of the phenyl may include, for example, linear or branched alkyl groups having 1 to 6 carbon atoms such as methyl and tert-butyl group; the alkoxy group as the substituent group of the phenyl may include, for example, linear or branched alkoxy groups having 1 to 6 carbon atoms such as methoxy and tert-butoxy group; and the halogen atom as the substituent group of the phenyl may include, for example, chlorine, bromine, and fluorine.

Specific examples of $R^{14}$ and $R^{15}$ are phenyl, p-tolyl, m-tolyl, 3,5-xylyl, p-tert-butylphenyl, p-methoxyphenyl, p-chlorophenyl, cyclopentyl, and cyclohexyl group.

The binaphthyl ring that is the basic skeleton of the compound defined by the general formula (6) may have a substituent group, and the substituent group may include, for example, alkyl groups such as methyl and tert-butyl group; alkoxy groups such as methoxy and tert-butoxy group; trialkylsilyl groups such as trimethylsilyl, triisopropylsilyl, and tert-butyldimethylsilyl group; and triarylsilyl groups such as triphenylsilyl group.

Another specific example of the optically active bisphosphine compound defined by $R^{10}R^{11}P$-Q-$PR^{12}R^{13}$ may be a compound defined by the following general formula (7).

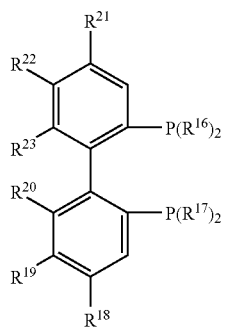

(7)

In the formula, $R^{16}$ and $R^{17}$ independently denote phenyl group optionally having a substituent group selected from a halogen atom, an alkyl group, and an alkoxy group, or denote cyclopentyl, or cyclohexyl group. $R^{18}$, $R^{19}$, $R^{20}$, $R^{21}$, $R^{22}$, and $R^{23}$ may be the same or different and independently denote a hydrogen atom, an alkyl group, an alkoxy group, an acyloxy group, a halogen atom, a haloalkyl group, or a dialkylamino group; two among $R^{18}$, $R^{19}$, and $R^{20}$ may form a methylene chain optionally having a substituent group or a (poly)methylenedioxy optionally having a substituent group; two among $R^{21}$, $R^{22}$, and $R^{23}$ may form a methylene chain optionally having a substituent group or a (poly)methylenedioxy optionally having a substituent group; $R^{20}$ and $R^{23}$ may form a methylene chain optionally having a substituent group or a (poly)methylenedioxy optionally having a substituent group; however, $R^{20}$ and $R^{23}$ are not a hydrogen atom.

In the above $R^{16}$ and $R^{17}$, the alkyl group as the substituent group of the phenyl may include, for example, linear or branched alkyl groups having 1 to 6 carbon atoms such as methyl and tert-butyl group; the alkoxy group as the substituent group of the phenyl may include, for example, linear or branched alkoxy groups having 1 to 6 carbon atoms such as methoxy and tert-butoxy group; and the halogen atom as the substituent group of the phenyl may include, for example, chlorine, bromine, and fluorine. A plurality of these substituent groups may be introduced into the phenyl group. Specific examples of $R^{16}$ and $R^{17}$ are phenyl, p-tolyl, m-tolyl, o-tolyl, 3,5-xylyl, 3,5-di-tert-butylphenyl, p-tert-butylphenyl, p-methoxyphenyl, 3,5-di-tert-butyl-4-methoxyphenyl, p-chlorophenyl, m-fluorophenyl, cyclopentyl, and cyclohexyl group.

The alkyl group denoted by $R^{18}$ to $R^{23}$ may include, for example, linear or branched alkyl groups having 1 to 6 carbon atoms such as methyl and tert-butyl group; the alkoxy group may include, for example, linear or branched alkoxy groups having 1 to 6 carbon atoms such as methoxy and tert-butoxy group; the acyloxy group may include, for example, acyloxy groups having 2 to 10 carbon atoms such as acetoxy, propanoyloxy, trifluoroacetoxy, and benzoyloxy group; the halogen atom may include, for example, chlorine, bromine, and fluorine; the haloalkyl group may include, for example, haloalkyl groups having 1 to 4 carbon atoms such as trifluoromethyl group; and the dialkylamino group may include, for example, dimethylamino and diethylamino group.

In the case where two of $R^{18}$, $R^{19}$, and $R^{20}$ form a methylene chain optionally having a substituent group and in the case where two of $R^{21}$, $R^{22}$, and $R^{23}$ form a methylene chain optionally having a substituent group, the methylene chain preferably includes, for example, methylene chains having 3 to 5 carbon atoms, and specific examples are trimethylene, tetramethylene, and pentamethylene group. The substituent group in the methylene chain optionally having a substituent group may be an alkyl group and a halogen atom, and specific examples are the above-mentioned alkyl groups having 1 to 6 carbon atoms and a fluorine atom.

In the case where two of $R^{18}$, $R^{19}$, and $R^{20}$ form a (poly)methylenedioxy group optionally having a substituent group and in the case where two of $R^{21}$, $R^{22}$, and $R^{23}$ form a (poly)methylenedioxy group optionally having a substituent group, specific examples of the (poly)methylenedioxy group are methylenedioxy, ethylenedioxy, and trimethylenedioxy group. The substituent group in the (poly)methylenedioxy may be an alkyl group and a halogen atom, and specific examples are the above-mentioned alkyl groups having 1 to 6 carbon atoms and a fluorine atom.

Specific examples of the optically active bisphosphine compound defined by the general formulas (6) and (7) are 2,2'-bis(diphenylphosphino)-1,1'-binaphthyl, 2,2'-bis[di(p-tolyl)phosphino]-1,1'-binaphthyl, 2,2'-bis[di(m-tolyl)phosphino]-1,1'-binaphthyl, 2,2'-bis[di(3,5-xylyl)phosphino]-1, 1'-binaphthyl, 2,2'-bis[di(p-tert-butylphenyl)phosphino]-1,1'-binaphthyl, 2,2'-bis[di(p-methoxyphenyl)phosphino]-1,1'-binaphthyl, 2,2'-bis[di(3,5-di-tert-butyl-4-methoxyphenyl)phosphino]-1,1'-binaphthyl, 2,2'-bis[di(cyclopentyl)phosphino]-1,1'-binaphthyl, 2,2'-bis[di(cyclohexyl)phosphino]-1,1'-binaphthyl, 2,2'-bis(diphenylphosphino)-5,5',6,6',7,7',8,8'-octahydro-1,1'-binaphthyl, 2,2'-bis(di-p-tolylphosphino)-5,5',6,6',7,7',8,8'-octahydro-1,1'-binaphthyl, 2,2'-bis(di-m-tolylphosphino)-5,5',6,6',7,7',8,8'-octahydro-1,1'-binaphthyl, 2,2'-bis(di-3,5-xylylphosphino)-5,5',6,6',7,7',8,8'-octahydro-1,1'-binaphthyl, 2,2'-bis(di-p-tert-butylphenylphosphino)-5,5',6,6',7,7',8,8'-octahydro-1,1'-binaphthyl, 2,2'-bis(di-p-methoxyphenylphosphino)-5,5',6,6',7,7',8,8'-octahydro-1,1'-binaphthyl, 2,2'-bis(di-p-chlorophenylphosphino)-5,5',6,6',7,7',8,8'-octahydro-1,1'-binaphthyl, 2,2'-bis(dicyclopentylphosphino)-5,5',6,6',7,7',8,8'-octahydro-1,1'-binaphthyl, 2,2'-bis(dicyclohexylphosphino)-5,5',6,6',7,7',8,8'-octahydro-1,1'-binaphthyl, ((4,4'-bi-1,3-benzodioxole)-5,5'-diyl)bis(diphenylphosphine) (hereinafter, referred to as segphos), ((4,4'-bi-1,3-benzodioxole)-5,5'-diyl)bis(bis(3,5-dimethylphenyl)phosphine), ((4,4'-bi-1,3-benzodioxole)-5,5'-diyl)bis(bis(3,5-di-tert-butyl-4-methoxyphenyl)phosphine), ((4,4'-bi-1,3-benzodioxole)-5,5'-diyl)bis(bis(4-methoxyphenyl)phosphine), ((4,4'-bi-1,3-benzodioxole)-5,5'-diyl)bis(dicyclohexylphosphine), ((4,4'-bi-1,3-benzodioxole)-5,5'-diyl)bis(bis(3,5-di-tert-butylphenyl)phosphine), 2,2'-bis(diphenylphosphino)-4,4',6,6'-tetramethyl-5,5'-dimethoxy-1,1'-biphenyl, 2,2'-bis(di-p-methoxyphenylphosphino)-4,4',6,6'-tetramethyl-5,5'-dimethoxy-1,1'-biphenyl, 2,2'-bis(diphenylphosphino)-4,4',6,6'-tetra(trifluoromethyl)-5,5'-dimethyl-1,1'-biphenyl, 2,2'-bis(diphenylphosphino)-4,6-di(trifluoromethyl)-4',6'-dimethyl-5'-methoxy-1,1'-biphenyl, 2-dicyclohexylphosphino)-2'-diphenylphosphino-4,4',6,6'-tetramethyl-5,5'-dimethoxy-1,1'-biphenyl, 2,2'-bis(diphenylphosphino)-6,6'-dimethyl-1,1'-biphenyl, 2,2'-bis(diphenylphosphino)-4,4',6,6'-tetramethyl-1,1'-biphenyl), 2,2'-bis(diphenylphosphino)-3,3',6,6'-tetramethyl-1,1'-biphenyl, 2,2'-bis(diphenylphosphino)-4,4'-difluoro-6,6'-dimethyl-1,1'-biphenyl, 2,2'-bis(diphenylphosphino)-4,4'-bis(dimethylamino)-6,6'-dimethyl-1,1'-biphenyl, 2,2'-bis(di-p-tolylphosphino)-6,6'-dimethyl-1,1'-biphenyl, 2,2'-bis(di-o-tolylphosphino)-6,6'-dimethyl-1,1'-biphenyl, 2,2'-bis(di-m-fluorophenylphosphino)-6,6'-dimethyl-1,1'-biphenyl, 1,11-bis(diphenylphosphino)-5,7-dihydrobenzo[c,e]oxepine, 2,2'-bis(diphenylphosphino)-6,6'-dimethoxy-1,1'-biphenyl, 2,2'-bis(diphenylphosphino)-5,5',6,6'-tetramethoxy-1,1'-biphenyl, 2,2'-bis(di-p-tolylphosphino)-6,6'-dimethoxy-1,1'-biphenyl, 2,2'-bis(diphenylphosphino)-4,4',5,5',6,6'-hexamethoxy-1,1'-biphenyl, 1,2-bis(2,5-dimethylphospholano)benzene, 1,2-bis(2,5-diethylphospholano)benzene, 1,2-bis(2,5-diisopropylphospholano)benzene, 1-(2,5-dimethylphospholano)-2-(diphenylphosphino)benzene; and 1,1'-bis(2,4-diethylphosphotano)ferrocene.

Additionally, specific examples of the optically active bisphosphine compound used in the invention may also include N,N-dimethyl-1-[1',2-bis(diphenylphosphino)ferrocenyl]ethyl amine, 2,3-bis(diphenylphosphino)butane, 1-cyclohexyl-1,2-bis(diphenylphosphino)ethane, 2,3-O-isopropylidene-2,3-dihydroxy-1,4-bis(diphenylphosphino)butane, 1,2-bis[(o-methoxyphenyl)phenylphosphino]ethane, 1,2-bis(2,5-dimethylphospholano) ethane, 5,6-bis(diphenylphosphino)-2-norbornene, N,N-bis(diphenylphosphino)-N,N'-bis(1-phenylethyl)ethylenediamine, 1,2-bis(diphenylphosphino)propane, and 2,4-bis(diphenylphosphino)pentane.

The catalyst used in the invention is a catalyst containing rhodium metal and an optically active bisphosphine, as described above, as catalytic components, and is a compound defined by the following general formula (4).

$$[Rh(L)_m(Y)_n]X \qquad (4)$$

In the formula (4), L denotes an optically active bisphosphine represented by $R^{10}R^{11}P-Q-PR^{12}R^{13}$; Y denotes a non-conjugated diene compound; X denotes a counter anion; m denotes an integer of 1 or 2; n denotes an integer of 1 or 2; however, in the case where m=1, n=0 or n=1; and in the case where m=2, n=0; $R^{10}$, $R^{11}$, $R^{12}$, and $R^{13}$ independently denote an aryl group optionally having a substituent group or a cycloalkyl group optionally having a substituent group; $R^{10}$ in combination with $R^{11}$ and/or $R^{12}$ in combination with $R^{13}$ may form a ring; and Q denotes a divalent arylene group optionally having a substituent group or a ferrocenediyl group.

The optically active bisphosphine denoted by L, that is $R^{10}R^{11}P-Q-PR^{12}R^{13}$, in the above formula, is as described above.

Next, the compound defined by the general formula (4) as an example of the catalyst containing rhodium metal and the optically active bisphosphine used in the invention will be described in more detail.

In the general formula (4), the non-conjugated diene compound denoted by Y may be cyclic or acyclic, and in the case where the non-conjugated diene compound is a cyclic non-conjugated diene compound, the compound may include monocyclic, polycyclic, condensed cyclic, or bicyclo compounds. Furthermore, the non-conjugated diene compound may include, for example, a non-conjugated diene compound having a substituent group, that is, a substituted non-conjugated diene compound, and the substituent group is not particularly limited as long as it does not negatively affect the production process of the invention. Preferable non-conjugated diene compounds are, for example, 1,5-cyclooctadiene, bicyclo[2,2,1]hepta-2,5-diene, and 1,5-hexadiene.

The counter anion denoted by X in the general formula (4) may include, for example, $BF_4$, $ClO_4$, $CF_3SO_3$ (hereinafter, abbreviated as OTf), $PF_6$, $SbF_6$, $B(3,5-(CF_3)_2C_6H_3)_4$, and $BPh_4$.

The compound defined by the general formula (4) used in the invention can be obtained by a conventionally known method as shown in the following scheme 1 under an inert gas atmosphere; or by reacting a commercially available rhodium-olefin complex with, for example, an optically active bisphosphine denoted by L in a solvent such as methanol, ethanol, isopropanol, butanol, toluene, or tetrahydrofuran and successively by counter-anion-exchange reaction with MX (M denotes a monovalent metal cation; and X denotes the same as described above) (accordingly, a compound (A) or (B) in the scheme 1 can be obtained), and optionally by further dissociating the olefin ligand by reacting the obtained compound with hydrogen gas (accordingly, a compound (C) in the scheme 1 can be obtained). The COD in the chemical formula denotes 1,5-cyclooctadiene (hereinafter, the same)

Scheme 1

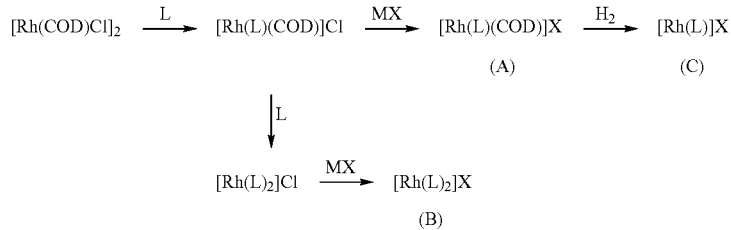

As shown in the following scheme 2, the compound defined by the general formula (4) used in the invention can be obtained also by reacting a rhodium-bisolefin complex previously subjected to counter-anion exchange reaction with an optically active bisphosphine denoted by L and optionally by further dissociating the olefin ligand with hydrogen gas.

Scheme 2

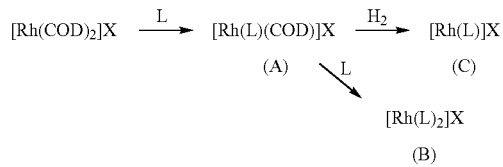

The added amount of the optically active bisphosphine denoted by L to the number of moles of the rhodium metal of the rhodium-olefin complex shown in the scheme 1 or the scheme 2 is 1.0 to 2.4 times, more preferably 1.05 to 2.2 times since part of the bisphosphine may possibly be oxidized.

In the present invention, the rhodium-olefin coordinated complex used for producing the compound as the catalyst defined by the general formula (4) may be various complexes depending on selected olefin ligands. However, for reasons of availability, a rhodium complex of 1,5-cyclooctadiene [Rh(COD)Cl]$_2$ and a rhodium complex of norbornadiene [Rh(NBD)Cl]$_2$ are particularly preferable. In the chemical formula, NBD denotes 2,5-norbornadiene (hereinafter, the same).

In the counter-anion-exchange reaction, for example, silver salt (AgX) is preferably used as MX in terms of the handling easiness.

The catalytic active species in the compound defined by the general formula (4) is [Rh(L)$_m$]X. However, a precursor thereof, for example, the compound (A): [Rh(L)(COD)]X in the above-mentioned scheme, may also be used in the production process of the invention.

The compounds defined by the general formula (4) such as compounds (A), (B), and (C) in the above-mentioned scheme can be used for the production process of the invention without further purification after being prepared as a catalyst. Furthermore, in the production process of the invention, the catalyst containing rhodium metal and an optically active bisphosphine can be used immediately after the preparation thereof. Specifically, a rhodium compound and an optically active bisphosphine are reacted to prepare the catalyst, and successively the above-mentioned diyne compound and alkynyl phosphorus compound may be added.

A reaction solvent used in the production process of the invention is not particularly limited as long as it does not cause any adverse effect on the reaction, and examples may include amides such as N,N-dimethylformamide, formamide, and N,N-dimethylacetamide; halohydrocarbons such as dichloromethane, 1,2-dichloroethane, chloroform, tetrachlorocarbon, and o-dichlorobenzene; aliphatic hydrocarbons such as pentane, hexane, heptane, octane, decane, and cyclohexane; aromatic hydrocarbons such as benzene, toluene, xylene; non-nucleophilic alcohols such as tert-butanol; ethers such as diethyl ether, diisopropyl ether, tert-butyl methyl ether, dimethoxyethane, ethylene glycol diethyl ether, tetrahydrofuran, 1,4-dioxane, and 1,3-dioxolane; and sulfoxides such as dimethyl sulfoxide. These reaction solvents may be used alone or in a suitable combination of two or more thereof.

In the production process of the invention, the usage of about 1 to 5 mol % of the catalyst containing rhodium metal and an optically active bisphosphine on the basis of conversion into rhodium metal is typically sufficient to the alkynyl compound defined by the formula of the reaction substrate (3-1) or (3-2).

In the production process of the invention, the reaction temperature for reacting the above-mentioned diyne compound and alkynyl compound naturally differs in accordance with the substrate used. However it is typically −20° C. to 100° C. and preferably in a range of 0° C. to 50° C. The reaction time naturally differs in accordance with the substrate used. However, it is typically 30 minutes to 30 hours and preferably 1 hour to 20 hours. The reaction is preferably carried out in an inert gas such as nitrogen or argon.

In addition, with respect to the phosphorus compound defined by the formula (1) or (3), a compound in which a in a group defined by the formula (R$^2$-1) or (R$^2$-2) is 0 can easily be produced by a conventional reaction (e.g. a method of reduction reaction) of a compound in which the corresponding a is 1.

On completion of the reaction, post-treatment which is routinely carried out in this kind of field such as filtration, silica gel column chromatography, or the like is carried out, and purification such as crystallization, distillation, and various kinds of chromatography may be carried out alone or in combination to obtain an aimed optically active phosphorus compound.

EXAMPLES

Hereinafter, the invention will be more specifically described by referring to the examples below. However, the invention is not limited to the illustrated examples.

The optical purity was measured by HPLC (high performance liquid chromatography) using an optically active column.

Examples 1 to 12

Preparation of Optically Active Biarylphosphine Oxide

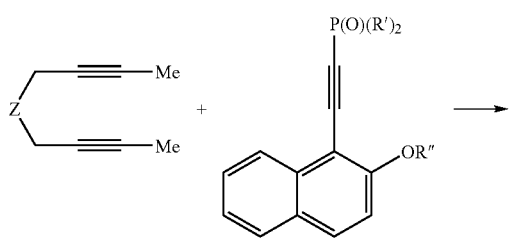

(* in the scheme represents axial asymmetry.)

According to the above reaction scheme (Me denotes a methyl group. Hereinafter, the same), optically active biarylphosphine oxides were produced. Under an argon atmosphere, (R)-H$_8$-BINAP (0.010 mmol), [Rh(COD)$_2$]BF$_4$ (0.010 mmol), and 1.0 mL of methylene chloride were placed into a schlenk tube, and stirred for 5 minutes. Then, hydrogen gas was introduced into the schlenk tube, and the mixture was stirred for 1 hour. Successively, the reaction mixture was vacuum concentrated and dried, and 1.0 mL of methylene chloride was added thereto. The diyne compound (0.20 to 0.60 mmol) and the monoyne compound (0.20 mmol) shown in the above reaction formula dissolved in 2 mL of methylene chloride solution were added to the solution, and stirred at room temperature for 1 hour. Next, the solvent was removed by distillation and purified by silica gel column chromatography to obtain target materials. The types of the groups denoted by Z, R', and R" in the reaction formula of each example (Et is ethyl; Ts is p-toluenesulfonyl; Cy is cyclohexyl; MOM is methoxymethyl; Bn is benzyl; and Ph is phenyl. Hereinafter, the same) and the results are shown in Table 1. The structural formula of (R)-H$_8$-BINAP is shown below.

TABLE 1

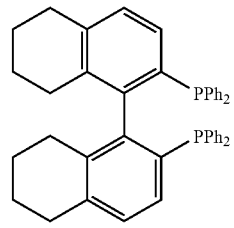

(R)-H$_8$-BINAP

| Example | Z | Number of moles of diyne | R' | R" | Yield | Optical purity and optical rotation |
|---|---|---|---|---|---|---|
| 1 | NTs | 0.20 mmol | OEt | MOM | 99% | 97% ee, (−) |
| 2 | NTs | 0.20 mmol | OEt | Bn | 99% | 97% ee. (−) |
| 3 | NTs | 0.20 mmol | OEt | Me | 96% | 96% ee. (+) |
| 4 | O | 0.30 mmol | OEt | Me | 99% | 97% ee, (−) |
| 5 | O | 0.30 mmol | OEt | Me | 99% | 97% ee, (−) |
| 6 | O | 0.60 mmol | Cy | Me | 99% | 98% ee, (+) |
| 7 | O | 0.30 mmol | Ph | Me | 92% | 91% ee, (−) |
| 8 | CH$_2$ | 0.30 mmol | OEt | Me | 99% | 98% ee. (−) |
| 9 | CH$_2$ | 0.30 mmol | Ph | Me | 86% | 91% ee, (−) |
| 10 | CH$_2$ | 0.60 mmol | Cy | Me | 70% | 96% ee, (+) |
| 11 | C(CO$_2$Me)$_2$ | 0.20 mmol | OEt | Me | 60% | 96% ee |
| 12 | C(CH$_2$OMe)$_2$ | 0.20 mmol | OEt | Me | 37% | 95% ee |

The catalyst amount in Example 5 was 1.0 mol %.

Example 13

Preparation of Optically Active Biarylphosphine Oxide

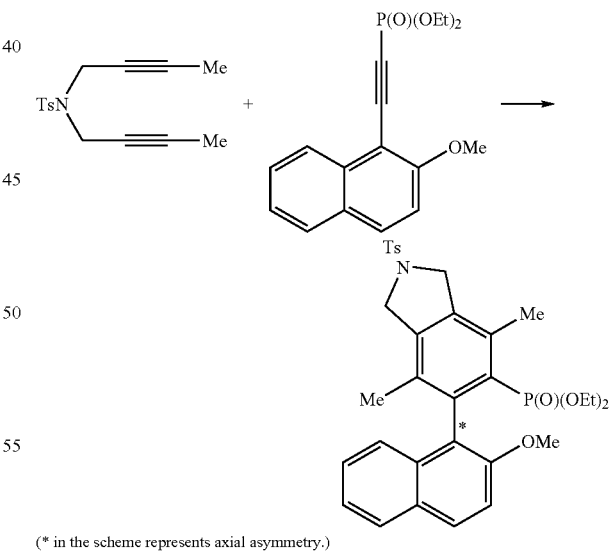

(* in the scheme represents axial asymmetry.)

According to the above reaction formula, an optically active biarylphosphine oxide was produced. Under an argon atmosphere, (R)-BINAP (0.010 mmol), [Rh(COD)$_2$]BF$_4$ (0.010 mmol), and 1.0 mL of methylene chloride were placed into a schlenk tube and stirred for 5 minutes. Then, hydrogen gas was introduced into the schlenk tube, and the mixture was stirred for 1 hour. Successively, the reaction solution was vacuum concentrated and dried, and 0.4 mL of methylene chloride was added thereto. The diyne compound (0.20 mmol) and the monoyne compound (0.20 mmol) dissolved in 1.0 mL of methylene chloride solution of were added to the solution, and stirred at room temperature for 1 hour. Next, the solvent was removed by distillation and purified by silica gel column chromatography to obtain the target material. The yield was 96%; optical purity was 96% ee; and the optical rotation was (−). The structural formula of (R)-BINAP is shown below.

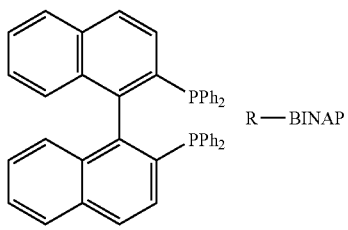

R—BINAP

Examples 14 to 18

Preparation of Optically Active Biarylphosphine Oxide

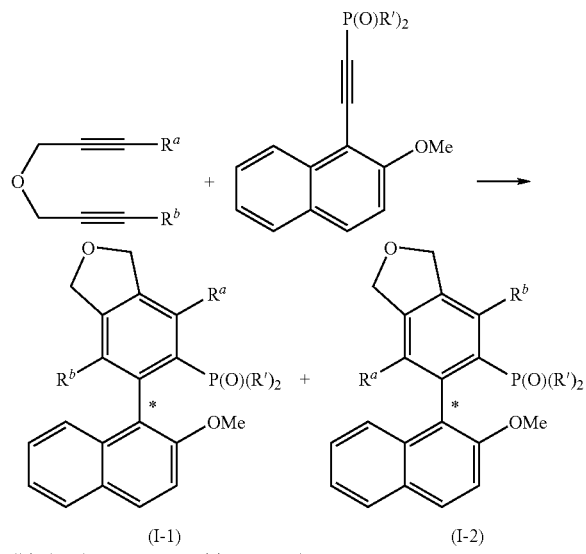

(I-1)  (I-2)

(* in the scheme represents axial asymmetry.)

According to the above reaction formula, optically active biarylphosphine oxides were produced. Under an argon atmosphere, (R)-H$_8$-BINAP (0.010 mmol), [Rh(COD)$_2$]BF$_4$ (0.010 mmol), and 1.0 mL of methylene chloride were placed into a schlenk tube and stirred for 5 minutes. Then, hydrogen gas was introduced into the schlenk tube, and the mixture was stirred for 1 hour. Successively, the reaction mixture was vacuum concentrated and dried, and 1.0 mL of methylene chloride was added thereto. The diyne compound (0.30 to 0.60 mmol) and the monoyne compound (0.20 mmol) dissolved in 2 mL of methylene chloride solution were added to the solution, and stirred at room temperature for 1 hour. Next, the solvent was removed by distillation and purified by silica gel column chromatography to obtain target materials. The results are shown in Table 2.

TABLE 2

| Example | R$^a$ | R$^b$ | Number of moles of diyne | R' | Yield (%) | Optical purity and optical rotation |
|---|---|---|---|---|---|---|
| 14 | Ph | Me | 0.30 mmol | OEt | (I-1) 80 (I-2) <1 | (I-1) 86% ee, (−) |
| 15 | Ph | H | 0.60 mmol | OEt | (I-1) 73 (I-2) <1 | (I-1) 96% ee, (−) |
| 16 | Ph | H | 0.60 mmol | Ph | (I-1) 34 (I-2) <1 | (I-1) 74% ee, (−) |
| 17 | Me | H | 0.60 mmol | Ph | (I-1) 54 (I-2) 46 | (I-1) 58% ee, (−) (I-2) 86% ee, (−) |
| 18 | Me | H | 0.30 mmol | OEt | (I-1) 65 (I-2) 35 | (I-1) 93% ee, (+) (I-2) 87% ee, (−) |

Examples 19 to 23

Preparation of Optically Active Biarylphosphine Oxide

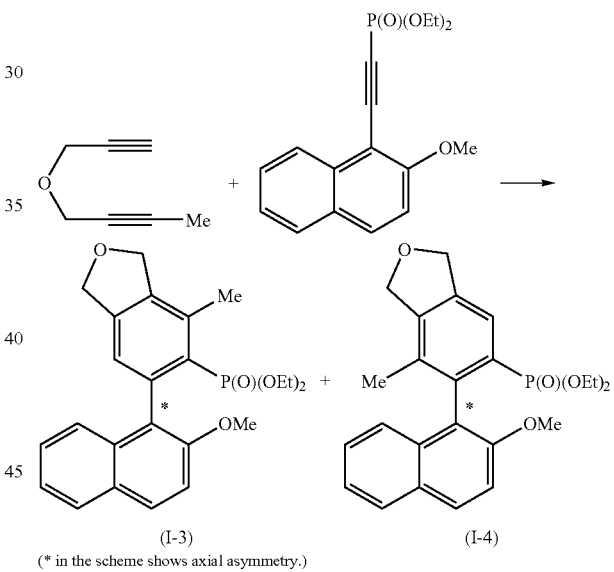

(I-3)  (I-4)

(* in the scheme shows axial asymmetry.)

According to the above reaction formula, optically active biarylphosphine oxides were produced. Under an argon atmosphere, optically active bisphosphines (0.010 mmol), [Rh(COD) 2]BF$_4$ (0.010 mmol), and 1.0 mL of methylene chloride were placed into a schlenk tube and stirred for 5 minutes. Then, hydrogen gas was introduced into the schlenk tube, and the mixture was stirred for 1 hour. Successively, the reaction mixture was vacuum concentrated and dried, and 1.0 mL of methylene chloride was added thereto. The diyne compound (0.30 mmol) and the monoyne compound (0.20 mmol) dissolved in 2 mL of methylene chloride solution were added to the solution and stirred at room temperature for 16 hours. Next, the solvent was removed by distillation and purified by silica gel column chromatography to obtain target materials. The results are shown in Table 3.

The structures of the optically active bisphosphines in the table are as follows.

TABLE 3

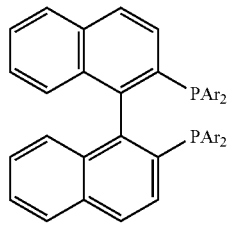

(R)-tol-BINAP
(Ar = 4-MeC$_6$H$_4$)
(R)-xyl-BINAP
(Ar = 3,5-di-MeC$_6$H$_3$)

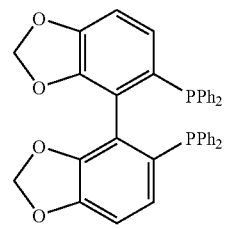

(R)-segphos

| Example | Optically active bisphosphine | Yield (I-3/I-4) | Optical purity and optical rotation |
|---|---|---|---|
| 19 | (R)-BINAP | 35% (81/19) | (I-3) 80% ee, (−) |
| 20 | (R)-tol-BINAP | 45% (94/6) | (I-3) 87% ee, (−) |
| 21 | (R)-xyl-BINAP | 15% (81/19) | |
| 22 | (R)-H$_8$-BINAP | 100% (65/35) | (I-3) 93% ee, (−) |
|  |  |  | (I-4) 87% ee, (−) |
| 23 | (R)-segphos | <10% | |

Example 24

Synthesis of (−)-1-[6-(diphenylphosphino)-4,7-dimethylindan-5-yl]-2-methoxynaphthalene

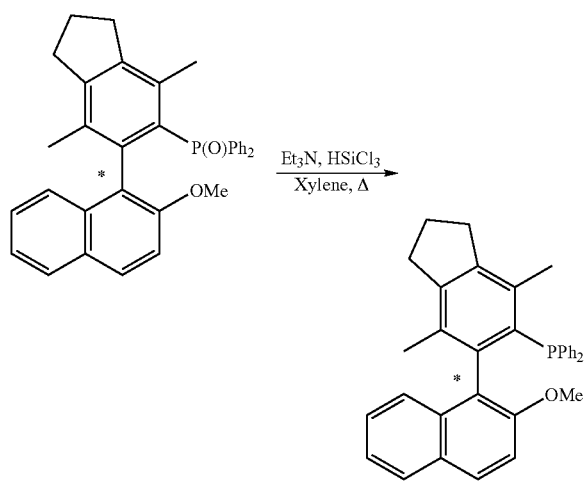

(−)-1-[6-(Diphenylphosphinoyl)-4,7-dimethylindan-5-yl]-2-methoxynaphthalene (800 mg, 1.59 mmol, 97% ee) was placed into a flask and the atmosphere in the flask was replaced with nitrogen. Triethylamine (4.4 mL, 31.8 mmol) was added to a solution of this naphthalene compound in xylene (40 mL), and cooled to 4° C. Further, trichlorosilane (800 μL, 7.95 mmol) was added dropwise, and the mixture was stirred for 30 minutes and then stirred at room temperature for 15 minutes. Further, the reaction mixture was heated to 110° C. and stirred for 3 hours. After the resulting reaction mixture was cooled to room temperature, diethyl ether (60 mL) and saturated aq. sodium bicarbonate (800 μL) were added, and the mixture was stirred for 30 minutes. The reaction mixture was filtered through Celite, and the filtrate was dried with sodium sulfate. After silica gel was added, the mixture was concentrated under reduced pressure. The residue was purified by silica gel chromatography to obtain the titled compound (744 mg, 96%, 97% ee).

Mp 166° C.; $[\alpha]_D^{25}$ 37.3° (c 1.00, CH$_2$Cl$_2$, 97% ee); $^1$H-NMR (CD$_2$Cl$_2$, 300 MHz) δ7.90-7.80 (m, 2H), 7.36-7.10 (m, 14H), 3.50 (s, 3H), 3.03 (t, J=7.4 Hz, 2H), 2.93 (t, J=8.0 Hz, 2H), 2.17 (dquint, J=7.3, 2.7, 2H), 1.77 (s, 3H), 1.75 (s, 3H); $^{31}$P-NMR (CD$_2$Cl$_2$, 121 MHz) δ=−11.0 (s)

Example 25

Synthesis of (−)-5-(diphenylphosphino)-6-(2-methoxynaphthalen-1-yl)-4,7-dimethyl-1,3-dihydroisobenzofuran

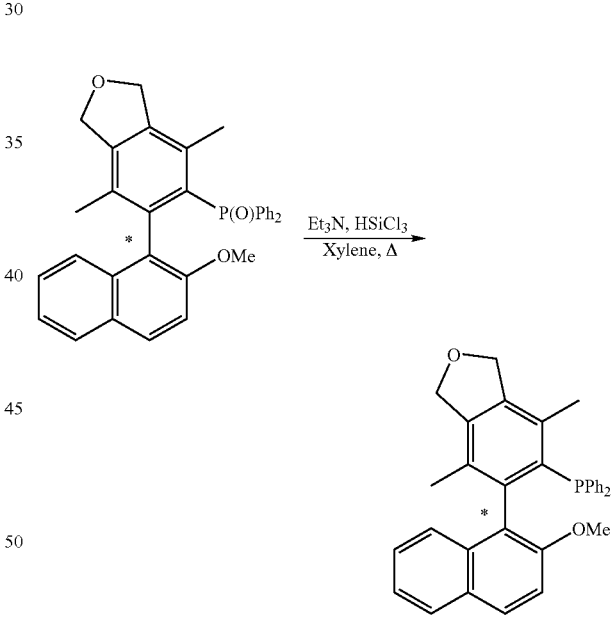

(−)-5-(Diphenylphosphinoyl)-6-(2-methoxynaphthalen-1-yl)-4,7-dimethyl-1,3-dihydroisobenzofuran (800 mg, 1.59 mmol, 92% ee) was placed into a flask and the atmosphere in the flask was replaced with nitrogen. Triethylamine (4.4 mL, 31.8 mmol) was added to a solution of this naphthalene compound in xylene (40 mL), and cooled to 4° C. Further, trichlorosilane (800 μL, 7.95 mmol) was added dropwise, and the mixture was stirred for 30 minutes and then stirred at room temperature for 15 minutes. Further, the reaction mixture was heated to 110° C. and stirred for 3 hours. After the resulting reaction mixture was cooled to room temperature, diethyl ether (60 mL) and saturated aq. sodium bicarbonate (800 μL) were added, and the mixture was stirred for 30 minutes. The reaction mixture was filtered through Celite, and after the filtrate was dried with sodium sulfate. After silica gel was added, the mixture was concentrated under reduced pressure. The residue was purified by silica gel chromatography to obtain the title compound (694 mg, 89%, 92% ee).

Mp 159° C.; [α]$_D^{25}$~39.0° (c 1.00, CH$_2$Cl$_2$, 92% ee); $^1$H-NMR (CD$_2$Cl$_2$, 300 MHz) δ7.91-7.79 (m, 2H), 7.35-7.10 (m, 14H), 5.22 (s, 2H), 5.12 (s, 2H), 3.50 (s, 3H), 1.73 (s, 3H), 1.68 (s, 3H); $^{31}$P-NMR (CD$_2$Cl$_2$, 121 MHz) δ=−11.9 (s)

Hereinafter, the structures and physical property data of the phosphorus compounds obtained in the examples are shown.

(−)-[6-(2-methoxynaphthalen-1-yl)-4,7-dimethyl-1,3-dihydro-isobenzofuran-5-yl]phosphonic acid diethyl ester

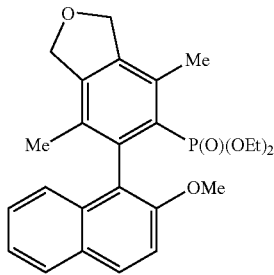

Colorless solid; melting point: 77.3-78.9° C.; [α]$^{25}_D$−22.8° (c 20.8, CHCl$_3$, 97% ee); IR (neat) 3300, 2900, 1580, 1210, 1020, 960 cm$^{-1}$; $^1$H NMR (CDCl$_3$, 300 MHz) δ7.87 (d, J=8.7 Hz, 1H), 7.74-7.82 (m, 1H), 7.35 (d, J=9.3 Hz, 1H), 7.21-7.30 (m, 2H), 7.04-7.11 (m 1H), 5.24 (s, 2H), 5.18 (s, 2H), 3.84 (s, 3H), 3.55-3.83 (m, 3H), 3.30-3.40 (m, 1H), 2.60 (s, 3H), 1.62 (s, 3H), 1.02 (t, J=7.2, 3H), 0.85 (t, J=7.2 Hz, 3H); $^{13}$C NMR (CDCl$_3$, 75 MHz) δ153.1, 141.8, 141.7, 140.3, 140.1, 138.7, 138.5, 133.7, 133.5, 133.4, 128.8, 128.63, 128.55, 128.5, 128.4, 127.5, 126.0, 125.8, 124.2, 123.32, 123.27, 122.8, 112.5, 74.20, 74.17, 74.1, 60.73, 60.71, 60.66, 60.6, 55.8, 18.81, 18.76, 16.1, 15.8, 15.7, 15.6, 15.5; $^{31}$P NMR (CDCl$_3$, 121 MHz) δ18.6; HRMS (FAB) calcd for C$_{25}$H$_{30}$O$_5$P [M+H]$^+$ 441.1831. found 441.1786. CHIRALPAK AD-H, hexane:2-PrOH=90:10, 1.0 mL/min, retention times: 8.56 min (major isomer) and 12.9 min (minor isomer).

(−)-[6-(2-methoxynaphthalen-1-yl)-4,7-dimethylindan-5-yl]phosphonic acid diethyl ester

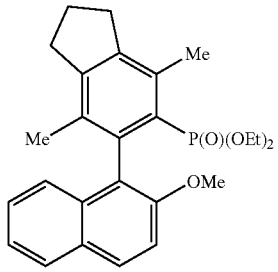

Pale yellow oil; [α]$^{25}_D$−24.2° (c 4.47, CHCl$_3$, 97% ee); IR (neat) 3350, 2850, 1230, 1040, 940 cm$^{-1}$; $^1$H NMR (CDCl$_3$, 300 MHz) δ7.85 (d, J=9.0 Hz, 1H), 7.73-7.80 (m, 1H), 7.34 (d, J=9.0 Hz, 1H), 7.15-7.30 (m, 2H), 7.03-7.15 (m, 1H), 3.84 (s, 3H), 3.52-3.80 (m, 3H), 3.18-3.34 (m, 1H), 3.01 (t, J=7.8 Hz, 2H), 2.96 (t, J=7.8 Hz, 2H), 2.63 (s, 3H), 2.13 (quint, J=7.8 Hz, 2H), 1.65 (s, 3H), 1.00 (t, J=7.2 Hz, 3H), 0.85 (t, J=7.2 Hz, 3H); $^{13}$C NMR (CDCl$_3$, 75 MHz) δ153.4, 147.2, 147.1, 143.7, 143.5, 138.7, 138.6, 136.0, 135.9, 133.9, 131.4, 131.2, 128.7, 128.3, 127.6, 126.7, 125.8, 125.0, 124.9, 124.8, 124.2, 122.9, 112.9, 60.74, 60.70, 60.67, 60.6, 56.1, 33.0, 32.85, 32.81, 23.5, 19.14, 19.08, 16.47, 16.46, 16.0, 15.9, 15.84, 15.78; $^{31}$P NMR (CDCl$_3$, 121 MHz) δ20.0; HRMS (FAB) calcd for C$_{26}$H$_{32}$O$_4$P [M+H]$^+$ 439.2038. found 439.2068. CHIRAL PAK AD-H, hexane:2-PrOH=95:5, 1.0 mL/min, retention times: 9.57 min (major isomer) and 13.1 min (minor isomer).

(+)-[6-(2-methoxynaphthalen-1-yl)-4,7-dimethyl-2-(p-toluenesulfonyl)-2,3-dihydro-1H-isoindol-5-yl] phosphonic acid diethyl ester

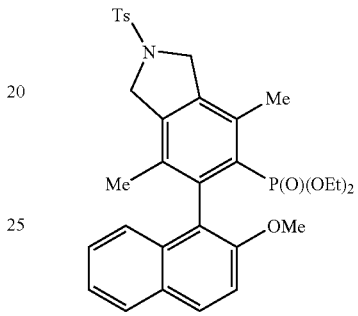

Colorless solid; melting point: 58.0-60.0° C.; [α]$^{25}_D$+0.71° (c 2.97, CHCl$_3$, 95% ee); IR (neat) 3300, 2900, 1240, 1010 cm$^{-1}$; $^1$H NMR (CDCl$_3$, 300 MHz) δ7.91-7.74 (m, 5H), 7.16-7.40 (m, 4H), 6.97 (d, J=7.5 Hz, 1H), 4.59 (m, 4H), 3.82 (s, 3H), 3.52-3.52 (m, 3H), 3.18-3.32 (m, 1H), 2.55 (s, 3H), 2.44 (s, 3H), 1.59 (s, 3H), 0.99 (t, J=7.2 Hz, 3H), 0.83 (t, J=7.2 Hz, 3H); $^{13}$C NMR (CDCl$_3$, 75 MHz) δ153.2, 143.6, 140.7, 140.6, 139.1, 139.0, 136.0, 135.8, 135.2, 135.0, 133.7, 133.4, 130.4, 130.2, 129.8, 128.6, 127.8, 127.5, 126.9, 126.1, 124.2, 123.2, 123.12, 123.09, 112.7, 61.6, 61.1, 61.00, 60.97, 60.9, 56.0, 54.19, 54.16, 54.1, 21.4, 18.8, 18.7, 16.13, 16.11, 16.0, 15.9, 15.8, 15.7; $^{31}$P NMR (CDCl$_3$, 121 MHz) δ18.0; HRMS (FAB) calcd for C$_{32}$H$_{37}$O$_6$NPS [M+H]$^+$ 594.2079. found 594.2047. CHIRALPAK AD-H, hexane:2-PrOH=80:20, 1.0 mL/min, retention times: 13.2 min (major isomer) and 18.7 min (minor isomer).

(−)-[6-(2-methoxynaphthalen-1-yl)-4,7-dimethyl-2-(p-toluenesulfonyl)-2,3-dihydro-1H-isoindol-5-yl] phosphonic acid diethyl ester

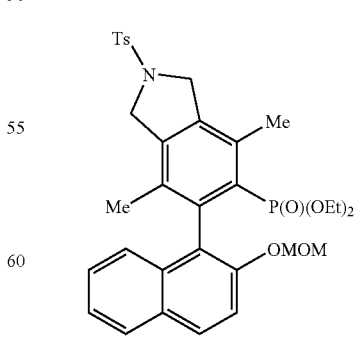

Pale yellow oil; [α]$^{25}_D$−12.4° (c 2.97, CHCl$_3$, 98% ee); IR (neat) 3350, 2850, 1430, 1320, 1220, 1140, 1010, 930 cm$^{-1}$; $^1$H NMR (CDCl$_3$, 300 MHz) δ7.75-7.88 (m, 4H), 7.52 (d, J=9.0 Hz, 1H), 7.37 (d, J=8.1 Hz, 2H), 7.18-7.34 (m, 2H), 6.98 (d, J=8.1 Hz, 1H), 5.20 (d, J=6.9 Hz, 1H), 5.05 (d, J=6.9 Hz, 1H), 4.73 (s, 2H), 4.67 (s, 2H), 3.47-3.80 (m, 3H), 3.35 (s, 3H), 3.15-3.35 (m, 1H), 2.55 (s, 3H), 2.45 (s, 3H), 1.61 (s, 3H), 0.96 (t, J=6.9 Hz, 3H), 0.88 (t, J=6.9 Hz, 3H); $^{13}$C NMR (CDCl$_3$, 75 MHz) δ151.4, 143.7, 140.4, 138.99, 138.95, 136.0, 135.0, 134.9, 133.8, 130.4, 130.2, 129.8, 129.4, 129.3, 128.9, 127.7, 127.5, 126.9, 126.0, 124.4, 124.32, 124.27, 123.5, 115.8, 94.7, 61.1, 61.0, 60.95, 60.89, 55.6, 54.13, 54.08, 54.0, 21.4, 18.8, 18.7, 16.1, 15.9, 15.81, 15.80, 15.7; $^{31}$P NMR (CDCl$_3$, 121 MHz) δ18.0; HRMS (FAB) calcd for C$_{33}$H$_{39}$O$_7$NPS [M+H]$^+$ 624.2185. found 624.2213. CHIRALPAK AD-H, hexane:2-PrOH=80:20, 1.0 mL/min, retention times: 13.2 min (major isomer) and 20.7 min (minor isomer).

(−)-[6-(2-benzyloxynaphthalen-1-yl)-4,7-dimethyl-2-(p-toluenesulfonyl)-2,3-dihydro-1H-isoindol-5-yl] phosphonic acid diethyl ester

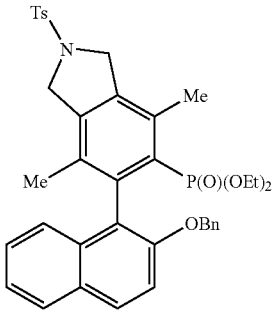

Colorless solid; melting point: 69.8-71.7° C.; [α]$^{25}_D$-14.9° (c 5.61, CHCl$_3$, 97% ee); IR (neat) 3300, 2900, 1590, 1330, 1240, 1160, 1010 cm$^{-1}$; $^1$H NMR (CDCl$_3$, 300 MHz) δ7.72-7.90 (m, 4H), 7.37 (d, J=8.1 Hz, 2H), 7.15-7.35 (m, 8H), 6.98-7.05 (m, 1H), 5.14 (s, 2H), 4.74 (s, 2H), 4.66 (s, 2H), 3.02-3.80 (m, 4H), 2.55 (s, 3H), 2.44 (s, 3H), 1.58 (s, 3H), 0.94 (t, J=7.2 Hz, 3H), 0.80 (t, J=7.2 Hz, 3H); $^{13}$C NMR (CDCl$_3$, 75 MHz) δ152.5, 143.7, 140.9, 140.7, 139.00, 138.99, 137.6, 135.1, 134.9, 133.8, 133.5, 130.5, 130.2, 129.9, 129.5, 128.9, 128.8, 128.2, 127.8, 127.5, 127.3, 127.0, 126.3, 126.1, 124.4, 124.2, 124.1, 123.3, 114.5, 70.5, 61.1, 61.04, 60.97, 54.2, 54.14, 54.11, 21.5, 18.8, 18.7, 16.20, 16.19, 15.9, 15.84, 15.77, 15.7; $^{31}$P NMR (CDCl$_3$, 121 MHz) δ18.0; HRMS (FAB) calcd for C$_{38}$H$_{41}$O$_6$NPS [M+H]$^+$ 670.2392. found 670.2445. CHIRALCEL OD-H, hexane:2-PrOH=90:10, 1.0 mL/min, retention times: 21.4 min (minor isomer) and 26.4 min (major isomer).

(−)-5-(diphenylphosphinoyl)-6-(2-methoxynaphthalen-1-yl)-4,7-dimethyl-1,3-dihydroisobenzofuran

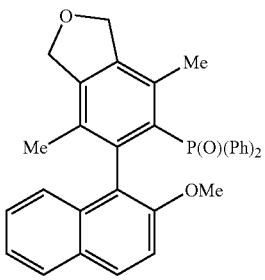

Colorless solid; melting point: 105.0-106.7° C.; [α]$^{25}_D$-147.2° (c 3.71, CHCl$_3$, 91% ee); IR (neat) 3300, 2850, 1590, 1440, 1250, 1160, 1070 cm$^{-1}$; $^1$H NMR (CDCl$_3$, 300 MHz) δ7.46-7.52 (m, 3H), 7.10-7.37 (m, 7H), 6.70-7.00 (m, 3H), 6.71-6.79 (m, 3H), 5.20 (s, 4H), 3.78 (s, 3H), 2.35 (s, 3H), 1.46 (s, 3H); $^{13}$C NMR (CDCl$_3$, 75 MHz) δ153.3, 141.91, 141.88, 139.6, 139.5, 139.4, 139.3, 136.2, 135.3, 135.2, 135.1, 134.9, 133.9, 133.7, 132.0, 131.3, 131.2, 130.8, 130.7, 130.64, 130.62, 130.2, 129.4, 129.00, 128.97, 128.8, 128.5, 127.7, 127.54, 127.52, 126.7, 126.5, 126.3, 124.7, 123.3, 122.0 120.9, 111.6, 74.50, 74.47, (74.4; 55.2, 19.9, 19.8, 16.2; $^{31}$P NMR (CDCl$_3$, 121 MHz) δ30.1; HRMS (FAB) calcd for C$_{33}$H$_{30}$O$_3$P [M+H]$^+$ 505.1933. found 505.1928. CHIRALPAK AD-H, hexane:2-PrOH=70:30, 1.0 mL/min, retention times: 14.2 min (major isomer) and 25.2 min (minor isomer).

(−)-1-[6-(diphenylphosphinoyl)-4,7-dimethylindan-5-yl]-2-methoxynaphthalene

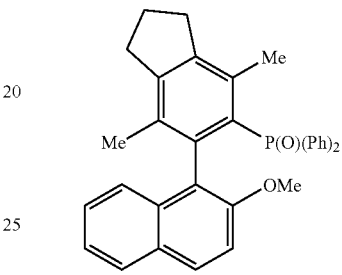

Colorless solid; melting point: 70.8-72.1° C.; [α]$^{25}_D$-143.9° (c 2.22, CHCl$_3$, 91% ee); IR (neat) 3350, 2900, 1590, 1440, 1250, 1160, 1090 cm$^{-1}$; $^1$H NMR (CDCl$_3$, 300 MHz) δ7.41-7.52 (m, 3H), 7.05-7.35 (m, 7H), 6.83-7.03 (m, 3H), 6.70-6.76 (m, 3H), 3.73 (s, 3H), 2.97 (t, J=6.9 Hz, 4H), 2.83 (s, 3H), 2.13 (quint, J=6.9 Hz, 2H), 1.50 (s, 3H); $^{13}$C NMR (CDCl$_3$, 75 MHz) δ153.3, 147.11, 147.07, 144.5, 144.3, 137.7, 137.3, 137.2, 137.0, 136.0, 135.7, 134.6, 134.0, 131.4, 131.2, 131.1, 130.8, 130.7, 130.5, 130.4, 130.0, 129.9, 129.70, 129.65, 128.6, 127.6, 127.44, 127.42, 126.4, 126.3, 125.1, 123.1, 122.3, 122.2, 111.7, 55.2, 33.1, 32.88, 32.86, 23.5, 20.3, 20.2, 16.39, 16.38; $^{31}$P NMR (CDCl$_3$, 121 MHz) δ31.0; HRMS (FAB) calcd for C$_{34}$H$_{32}$O$_2$P [M+H]$^+$ 503.2140. found 503.2165. CHIRALPAK AD-H, hexane:2-PrOH=80:20, 1.0 mL/min, retention times: 7.07 min (major isomer) and 19.0 min (minor isomer).

(S)-(+)-5-(dicyclohexylphosphinoyl)-6-(2-methoxynaphthalen-1-yl)-4,7-dimethyl-1,3-dihydroisobenzofuran

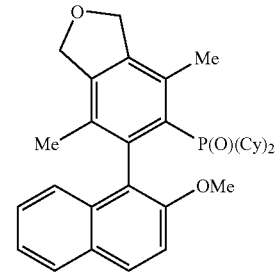

Colorless solid; melting point: 279° C. (decomposed): [α]$^{25}_D$-8.83° (c 4.61, CHCl$_3$, 98% ee); IR (neat) 2800, 1590, 1440, 1240, 1140, 1060 cm$^{-1}$; $^1$H NMR (CDCl$_3$, 300 MHz) δ7.87 (d, J=9.0 Hz, 1H), 7.78 (d, J=7.5 Hz, 1H), 7.31 (d, J=9.0 Hz, 1H), 7.15-7.28 (m, 2H), 7.01 (d, J=8.1 Hz, 1H), 5.23 (s, 2H), 5.21 (s, 2H), 3.85 (s, 3H), 2.44 (s, 3H), 0.92-1.98 (m, 25H); $^{13}$C NMR (CDCl$_3$, 75 MHz) δ153.2, 140.8, 140.7, 138.8, 138.7, 133.7, 130.7, 129.7, 129.0, 128.7, 128.0, 125.4, 124.8, 123.1, 123.0, 122.8, 112.1, 74.6, 74.4, 58.0, 55.6, 40.4, 40.2, 39.6, 39.3, 29.6, 27.0, 26.80, 26.76, 26.62, 26.56, 26.51, 26.46, 25.8, 25.7, 19.63, 19.60, 18.3, 16.4; $^{31}$P NMR (CDCl$_3$, 121 MHz) δ-16.9; HRMS (FAB) calcd for C$_{33}$H$_{42}$O$_3$P [M+H]$^+$ 517.2872. found 517.2881. CHIRALPAK AD-H, hexane:2-PrOH=95:5, 1.2 mL/min, retention times: 25.1 min (minor isomer) and 32.0 min (major isomer).

(+)-1-[6-(dicyclohexylphosphinoyl)-4,7-dimethylindan-5-yl]-2-methoxynaphthalene

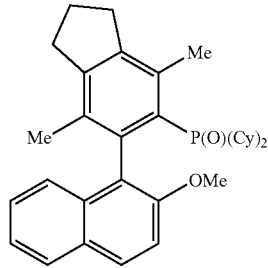

Colorless solid; melting point: 272° C. (decomposed): $[α]^{25}_D$–6.17° (c 4.20, CHCl$_3$, 96% ee); IR (neat) 2900, 1590, 1440, 1260, 1150, 1080 cm$^{-1}$; $^1$H NMR (CDCl$_3$, 300 MHz) δ7.83 (d, J=9.0 Hz, 1H), 7.76 (d, J=7.5 Hz, 1H), 7.29 (d, J=9.0 Hz, 1H), 7.12-7.26 (m, 2H), 7.01 (d, J=8.1 Hz, 1H), 3.85 (s, 3H), 2.98 (t, J=4.5 Hz, 4H), 2.41 (s, 3H), 2.15 (quint, J=4.5 Hz, 2H), 0.78-1.90 (m, 25H); $^{13}$C NMR (CDCl$_3$, 75 MHz) δ153.2, 145.80, 145.77, 143.4, 133.9, 132.4, 128.7, 128.3, 127.8, 125.2, 124.9, 124.5, 124.4, 122.5, 112.2, 55.6, 45.7, 40.7, 40.4, 39.9, 39.5, 32.9, 30.8, 27.1, 27.04, 26.99, 26.9, 26.84, 26.80, 26.75, 26.64, 26.59, 26.54, 26.0, 25.74, 25.72, 23.4, 19.90, 19.87, 18.3, 16.5; $^{31}$P NMR (CDCl$_3$, 121 MHz) δ-17.3; HRMS (FAB) calcd for C$_{34}$H$_{44}$O$_2$P [M+H]$^+$ 515.3079. found 515.3074. CHIRALPAK AD-H, hexane:2-PrOH=95:5, 1.0 mL/min, retention times: 5.71 min (minor isomer) and 10.2 min (major isomer).

(−)-[6-(2-methoxynaphthalen-1-yl)-7-methyl-4-phenyl-1,3-dihydroisobenzofuran-5-yl]phosphonic acid diethyl ester

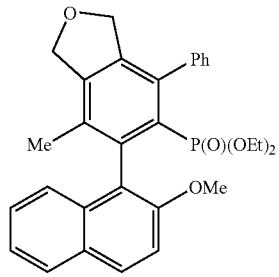

Colorless solid; melting point: 54.1-56.0° C.; $[α]^{25}_D$–40.4° (c 3.13, CHCl$_3$, 86% ee); IR (neat) 3300, 2800, 1580, 1240, 1020 cm$^{-1}$; $^1$H NMR (CDCl$_3$, 300 MHz) δ7.89 (d, J=9.0 Hz, 1H), 7.60-7.84 (m, 1H), 7.26-7.50 (m, 8H), 7.19-7.26 (m, 1H), 5.22 (s, 2H), 4.91 (d, J=13.2 Hz, 1H), 4.86 (d, J=13.2 Hz, 1H), 3.92 (s, 3H), 3.33-3.48 (m, 2H), 2.93-3.08 (m, 2H), 1.72 (s, 3H), 0.67 (t, J=6.9 Hz, 3H), 0.64 (t, J=6.9 Hz, 3H); $^{13}$C NMR (CDCl$_3$, 75 MHz) δ153.97, 153.95, 141.94, 141.90, 140.64, 140.58, 140.5, 140.3, 138.9, 138.7, 138.5, 138.4, 133.7, 131.2, 131.0, 129.2, 129.1, 128.8, 128.7, 128.6, 127.7, 127.60, 127.58, 127.0, 126.6, 126.1, 125.0, 123.18, 123.16, 123.1, 113.2, 74.78, 74.76, 74.4, 74.3, 60.64, 60.58, 60.5, 56.4, 16.57, 16.55, 15.7, 15.60, 15.58, 15.5; $^{31}$P NMR (CDCl$_3$, 121 MHz) δ16.7; HRMS (FAB) calcd for C$_{30}$H$_{32}$O$_5$P [M+H]$^+$ 503.1987. found 503.2003. CHIRALPAK AD-H, hexane:2-PrOH=95:5, 1.0 mL/min, retention times: 15.0 min (major isomer) and 45.3 min (minor isomer).

(−)-[6-(2-methoxynaphthalen-1-yl)-4-phenyl-1,3-dihydroisobenzofuran-5-yl]phosphonic acid diethyl ester

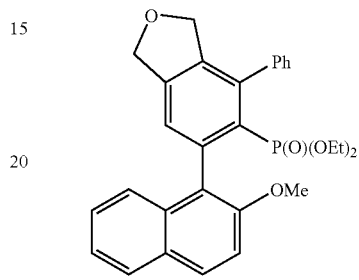

Colorless solid; melting point: 123.1-125.1° C.; $[α]^{25}_D$–14.9° (c 2.57, CHCl$_3$, 96% ee); IR (neat) 2850, 1590, 1430, 1220, 1050, 940 cm$^{-1}$; $^1$H NMR (CDCl$_3$, 300 MHz) δ7.88 (d, J=9.0 Hz, 1H), 7.83-7.77 (m, 1H), 7.47-7.26 (m, 9H), 7.11 (d, J=3.9 Hz, 1H), 5.21 (s, 2H), 4.81 (d J=12.6 Hz, 1H), 4.81 (d, J=12.6 Hz, 1H), 3.91 (s, 3H), 3.37-3.52 (m, 2H), 2.89-3.11 (m, 2H), 0.68 (t, J=6.9 Hz, 3H), 0.63 (t, J=6.9 Hz, 3H); $^{13}$C NMR (CDCl$_3$, 75 MHz) δ153.8, 142.5, 142.4, 141.4, 141.2, 141.1, 140.9, 140.20, 140.15, 139.3, 139.1, 133.7, 129.03, 128.96, 128.82, 128.81, 128.7, 128.6, 127.70, 127.66, 127.6, 127.3, 126.4, 126.1, 125.70, 125.65, 125.6, 124.4, 124.1, 123.2, 113.2, 74.11, 74.09, 73.89, 73.86, 60.8, 60.74, 60.72, 60.6, 45.5, 30.9, 15.7, 15.60, 15.57, 15.5; $^{31}$P NMR (CDCl$_3$, 121 MHz) δ16.7; HRMS (FAB) calcd for C$_{29}$H$_{30}$O$_5$P [M+H]$^+$ 489.1831. found 489.1783. CHIRALPAK AD, hexane:2-PrOH=85:15, 1.0 mL/min, retention times: 7.00 min (major isomer) and 46.0 min (minor isomer).

(+)-[6-(2-methoxynaphthalen-1-yl)-4-methyl-1,3-dihydroisobenzofuran-5-yl]phosphonic acid diethyl ester

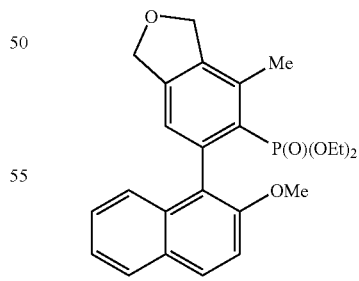

Colorless solid; melting point: 68.0-69.9° C.; $[α]^{25}_D$+7.99° (c 1.37, CHCl$_3$, 93% ee); IR (neat) 2800, 1570, 1220, 1000 cm$^{-1}$; $^1$H NMR (CDCl$_3$, 300 MHz) δ7.86 (d, J=9.0 Hz, 1H), 7.75-7.81 (m, 1H), 7.32 (d, J=9.0 Hz, 1H), 7.17-7.30 (m, 3H), 6.93 (d, J=3.6 Hz, 1H), 5.20 (s, 2H), 5.18 (s, 2H), 3.84 (s, 3H), 3.60-3.84 (m, 3H), 3.22-3.40 (m, 1H), 2.63 (s, 3H), 1.02 (t, J=6.9 Hz, 3H), 0.85 (t, J=6.9 Hz, 3H); $^{13}$C NMR (CDCl$_3$, 75 MHz) δ153.3, 150.1, 149.9, 142.41, 142.37, 141.3, 141.2, 139.4, 139.1, 136.8, 136.6, 133.9, 128.9, 128.7, 128.6, 128.4, 127.7, 126.05, 125.97, 125.9, 125.1, 123.1, 122.7, 122.4, 112.9, 74.8, 74.14, 74.12, 73.64, 73.61, 61.24, 61.17, 61.13, 61.05, 56.2, 19.23, 19.18, 18.3, 16.0, 15.9, 15.8, 15.7; $^{31}$P NMR (CDCl$_3$, 121 MHz) δ18.2; HRMS (FAB) calcd for C$_{24}$H$_{28}$O$_5$P [M+H]$^+$ 427.1674. found 427.1650. CHIRAL-PAK AD, hexane:2-PrOH=80:20, 1.0 mL/min, retention times: 6.60 min (major isomer) and 11.8 min (minor isomer).

(−)-[6-(2-methoxynaphthalen-1-yl)-7-methyl-1,3-dihydro isobenzofuran-5-yl]phosphonic acid diethyl ester

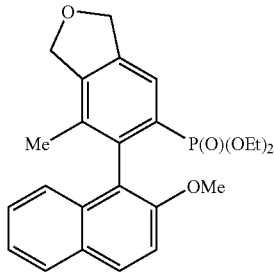

Colorless solid; melting point: 136.1-138.0° C.; [α]$^{25}_D$ −1.26° (c 1.44, CHCl$_3$, 87% ee); IR (neat); 2900, 1590, 1449, 1240, 1010, 800 cm$^{-1}$; $^1$H NMR (CDCl$_3$, 300 MHz) δ7.85-8.00 (m, 2H), 7.75-7.83 (m, 1H), 7.36 (d, J=9.3 Hz, 1H), 7.21-7.33 (m, 2H), 6.98-7.09 (m, 1H), 5.27 (s, 2H), 5.19 (s, 2H), 3.87 (s, 3H), 3.65-3.78 (m, 1H), 3.44-3.61 (m, 3H), 1.75 (s, 3H), 0.97 (t, J=7.2 Hz, 3H), 0.68 (t, J=7.2 Hz, 3H); $^{13}$C NMR (CDCl$_3$, 75 MHz) δ154.2, 143.2, 143.1, 139.0, 138.9, 137.9, 137.7, 133.8, 132.4, 132.2, 130.0, 129.6, 128.6, 127.7, 127.5, 126.1, 125.0, 124.7, 124.5, 123.2, 121.2, 121.1, 112.7, 74.30, 74.26, 73.6, 61.5, 61.43, 61.38, 61.3, 56.0, 16.27, 16.26, 16.0, 15.9, 15.5, 15.4; $^{31}$P NMR (CDCl$_3$, 121 MHz) δ19.0; HRMS (FAB) calcd for C$_{24}$H$_{28}$O$_5$P [M+H]$^+$ 427.1674. found 427.1631. CHIRALPAK AD-H, hexane:2-PrOH=85:15, 1.0 mL/min, retention times: 6.8 min (major isomer) and 10.5 min (minor isomer).

(−)-5-(diphenylphosphinoyl)-6-(2-methoxynaphthalen-1-yl)-4-phenyl-1,3-dihydroisobenzofuran

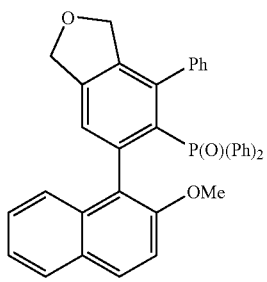

Colorless solid; melting point: 129.1-131.0° C.; [α]$^{25}_D$ −31.1° (c 1.19, CHCl$_3$, 74% ee); IR (neat) 3300, 2900, 1590, 1430, 1240, 1180, 1150, 680 cm$^{-1}$; $^1$H NMR (CDCl$_3$, 300 MHz) δ7.50-7.60 (m, 2H), 7.38-7.47 (m, 2H), 7.11-7.32 (m, 3H), 6.90-7.11 (m, 10H), 6.73-6.90 (m, 5H), 5.23 (s, 2H), 4.86 (d, J=12.9 Hz, 1H), 4.79 (d, J=12.9 Hz, 1H), 3.90 (s, 3H); $^{13}$C NMR (CDCl$_3$, 75 MHz) δ153.5, 142.8, 142.68, 142.65, 141.3, 141.1, 140.0, 139.9, 138.24, 138.18, 136.1, 135.6, 134.7, 133.5, 131.9, 130.43, 130.39, 130.3, 130.2, 130.1, 129.4, 129.3, 128.494, 128.491, 127.02, 126.97, 126.94, 126.85, 126.8, 126.7, 126.4, 125.6, 124.8, 124.6, 123.3, 111.9, 73.9, 55.6; $^{31}$P NMR (CDCl$_3$, 121 MHz) δ22.4; HRMS (FAB) calcd for C$_{37}$H$_{30}$O$_3$P [M+H]$^+$ 553.1933. found 553.1961. CHIRALPAK AD, hexane:2-PrOH=80:20, 1.0 mL/min, retention times: 8.84 min (major isomer) and 62.4 min (minor isomer).

(−)-5-(diphenylphosphinoyl)-6-(2-methoxynaphthalen-1-yl)-4-methyl-1,3-dihydroisobenzofuran

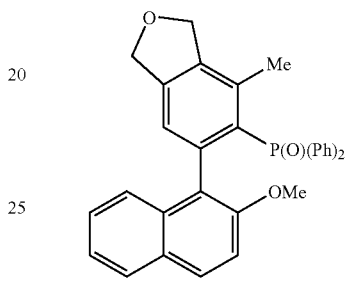

Yellow oil; [α]$^{25}_D$−540.1° (c 2.85, CHCl$_3$, 58% ee); IR (neat) 2850, 1590, 1440, 1250, 1150, 1060 cm$^{-1}$; $^1$H NMR (CDCl$_3$, 300 MHz) δ7.45-7.61 (m, 3H), 7.14-7.38 (m, 7H), 6.87-7.08 (m, 3H), 6.68-6.87 (m, 4H), 5.17 (s, 4H), 3.74 (s, 3H), 2.41 (s, 3H); $^{13}$C NMR (CDCl$_3$, 75 MHz) δ153.1, 142.3, 140.6, 140.4, 140.1, 140.0, 138.2, 138.0, 135.6, 135.0, 134.3, 133.9, 133.6, 131.5, 131.4, 131.3, 131.0, 130.9, 130.8, 130.7, 130.3, 130.2, 130.1, 129.8, 128.4, 127.7, 127.5, 127.4, 126.6, 126.5, 126.4, 125.4, 123.64, 123.58, 123.2, 123.0, 122.9, 111.7, 74.1, 73.7, 73.6, 55.3, 20.1, 20.0; $^{31}$P NMR (CDCl$_3$, 121 MHz) δ0.0; HRMS (FAB) calcd for C$_{32}$H$_{28}$O$_3$P [M+H]$^+$ 491.1776. found 491.1760. CHIRALPAK AD, hexane:2-PrOH=80:20, 1.0 mL/min, retention times: 11.4 min (major isomer) and 49.3 min (minor isomer).

(−)-6-(diphenylphosphinoyl)-5-(2-methoxynaphthalen-1-yl)-4-methyl-1,3-dihydroisobenzofuran

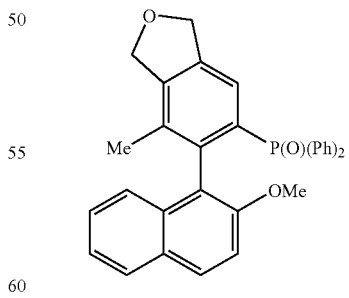

Colorless oil; [α]$^{25}_D$−49.1° (c 0.665, CHCl$_3$, 86% ee); IR (neat) 2800, 1570, 1220, 1000 cm$^{-1}$; $^1$H NMR (CDCl$_3$, 300 MHz) δ7.51-7.64 (m, 3H), 7.34-7.46 (m, 2H), 7.00-7.34 (m, 10H), 6.95 (d, J=9.3 Hz, 1H), 6.90 (d, J=8.1 Hz, 1H), 5.20 (s, 4H), 3.65 (s, 3H), 1.68 (s, 3H); $^{13}$C NMR (CDCl$_3$, 75 MHz) δ154.1, 143.0, 142.6, 138.0, 137.8, 133.4, 132.8, 131.7, 131.6, 131.4, 131.3, 130.79, 130.75, 130.6, 130.1, 128.3, 127.7, 127.52, 127.49, 127.3, 127.2, 126.1, 124.8, 124.5, 124.3, 123.1, 120.1, 120.0, 111.8, 74.3, 73.6, 55.4; $^{31}$P NMR (CDCl$_3$, 121 MHz) δ28.7; HRMS (FAB) calcd for C$_{32}$H$_{28}$O$_3$P [M+H]$^+$ 491.1776. found 491.1779. CHIRAL-PAK AD, hexane:2-PrOH=80:20, 1.0 mL/min, retention times: 10.6 min (major isomer) and 16.9 min (minor isomer).

Example 26

Hydrosilylation of Styrene

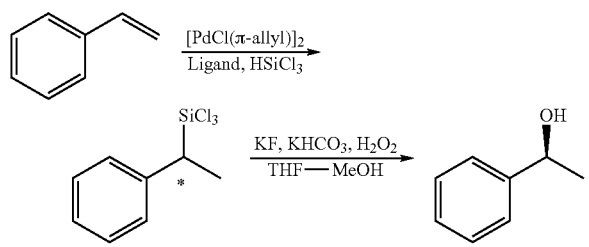

(–)-1-[6-(Diphenylphosphino)-4,7-dimethylindan-5-yl]-2-methoxynaphthalene (26.6 mg, 0.0547 mmol, 97% ee) and allylpalladium chloride dimer (5.0 mg, 0.0137 mmol) were placed into a flask and the atmosphere in the flask was replaced with nitrogen. Toluene (1 mL) was added to dissolve them, and the solution was stirred at 30° C. for 30 minutes. After the prepared complex was transferred into a four-necked flask, toluene (26.3 mL) and styrene (3.1 mL=2.85 g, 27.3 mmol) were added thereto, and the mixture was stirred for 15 minutes. Further, a toluene (27.3 mL) solution of HSiCl$_3$ (4.44 g, 32.3 mmol) was added dropwise over 1 hour, and then the mixture was stirred for 15 hours. HSiCl$_3$ and toluene was removed by using a Liebig condenser. 4.3 g of silylated substance (17.7 mmol, 65%) was obtained after distillation under reduced pressure.

Boiling point: 120-123° C./20 Torr

KF (6.2 g, 106.2 mmol) and KHCO$_3$ (21.3 g, 212.4 mmol) were placed into a round flask, suspended in MeOH-THF (1:1, 85 mL), and cooled with ice water. To the suspension 4.2 g of the above obtained silylated substance (17.7 mmol) was added dropwise, and then the mixture was stirred still being cooled with ice water for 1 hour, and at room temperature for another 1 hour. Then, the mixture was cooled with ice water, and H$_2$O$_2$ (30% aqueous solution, 17.7 mL) was added dropwise still being kept in the bath overnight with stirring. The mixture was cooled with ice water, and Na$_2$S$_2$O$_3$.5H$_2$O (22.0 g, 88.5 mmol) was added thereto. The mixture was further stirred still being cooled with ice water for 1 hour and at room temperature for another 1 hour. The reaction mixture was filtered through Celite, and then concentrated in vacuo. After the remaining residue was extracted with EtOAc, the combined organic layers were washed with water and brine, dried with Na$_2$SO$_4$, and concentrated in vacuo. 1.6 g of sec-phenethyl alcohol (12.9 mmol, 73%) was obtained after distillation under reduced pressure.

Boiling point: 104° C./20 Torr The optical purity of the obtained alcohol was 60% ee (S configuration). Analytical method of optical purity: Column; Chirasil-Dex CB, Injector temperature; 250° C., Detector temperature; 250° C., Oven; 115° C.

Example 27

Hydrosilylation of Styrene (–)-5-(diphenylphosphino)-6-(2-methoxynaphthalen-1-yl)-4,7-dimethyl-1,3-dihydroisobenzofuran (26.7 mg, 0.0547 mmol, 92% ee) and allylpalladium chloride dimer (5.0 mg, 0.0137 mmol) were placed into a flask and the atmosphere in the flask was replaced with nitrogen. Toluene (1 mL) was added to dissolve them, and the solution was stirred at 30° C. for 30 minutes. After the prepared complex was transferred into a four-necked flask, toluene (26.3 mL) and styrene (3.1 mL=2.85 g, 27.3 mmol) were added thereto, and the mixture was stirred for 15 minutes. Further, a toluene (27.3 mL) solution of HSiCl$_3$ (4.44 g, 32.3 mmol) was added dropwise over 1 hour, and then the mixture was stirred for 15 hours. HSiCl$_3$ and toluene was removed by using a Liebig condenser. 4.3 g of the silylated substance (17.5 mmol, 64%) was obtained after distillation under reduced pressure.

Boiling point: 120-123° C./20 Torr

KF (5.5 g, 94.2 mmol) and KHCO$_3$ (18.9 g, 188.4 mmol) were placed into a round flask, suspended in MeOH-THF (1:1, 75 mL), and cooled with ice water. To the suspension 3.8 g of the obtained silylated substance (15.7 mmol) was added dropwise, and then the mixture was stirred still being cooled with ice water for 1 hour and at room temperature for another 1 hour. Then, the mixture was cooled with ice water, and H$_2$O$_2$ (30% aqueous solution, 15.7 mL) was added dropwise still being kept in the bath overnight with stirring. The mixture was cooled with ice water, and Na$_2$S$_2$O$_3$.5H$_2$O (19.5 g, 78.6 mmol) was added thereto. The mixture was further stirred still being cooled with ice water for 1 hour and at room temperature for another 1 hour. The reaction mixture was filtered through Celite, and then concentrated in vacuo. After the remaining residue was extracted with EtOAc, the combined organic layers were washed with water and brine, dried with Na$_2$SO$_4$, and concentrated in vacuo. 1.4 g of sec-phenethyl alcohol (11.5 mmol, 73%) was obtained after distillation under reduced pressure.

Boiling point: 104° C./20 Torr The optical purity of the obtained alcohol was 58% ee (S configuration).

Example 28

Hydrosilylation of 1-octene

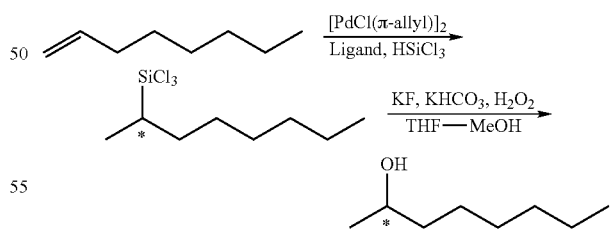

(–)-1-[6-(Diphenylphosphino)-4,7-dimethylindan-5-yl]-2-methoxynaphthalene (26.6 mg, 0.0547 mmol, 97% ee) and allylpalladium chloride dimer (5.0 mg, 0.0137 mmol) were placed into a flask and the atmosphere in the flask was replaced with nitrogen. Toluene (1 mL) was added to dissolve them, and the solution was stirred at 30° C. for 30 minutes. After the bath was set at 40° C., toluene (3 mL) and 1-octene (3.1 g, 27.3 mmol) were added thereto, and the mixture was stirred for 30 minutes. Further, HSiCl$_3$ (4.44 g, 32.3 mmol)

was added dropwise, and then the mixture was stirred for 24 hours. Analysis of the reaction mixture revealed that 2-trichlorosilyloctane/1-trichlorosilyloctane=76/24. HSiCl$_3$ and toluene was removed by using a Liebig condenser. 1.6 g of silylated substance (6.6 mmol, 24%, 2-trichlorosilyloctane/1-trichlorosilyloctane=77/23) was obtained after distillation under reduced pressure.

Boiling point: 120-123° C./25 Torr

KF (1.9 g, 32.7 mmol) and KHCO$_3$ (6.4 g, 63.9 mmol) were placed into a round flask, suspended in MeOH-THF (1:1, 26 mL), and cooled with ice water. 1.3 g of the above obtained silylated substance (5.3 mmol) was added dropwise, and then the mixture was stirred still being cooled with ice water for 1 hour, and at room temperature for another 1 hour. Then, the mixture was cooled with ice water, and H$_2$O$_2$ (30% aqueous solution, 5.3 mL) was added dropwise still being kept in the bath overnight with stirring. The mixture was cooled with ice water, and Na$_2$S$_2$O$_3$.5H$_2$O (6.6 g, 26.6 mmol) was added thereto. The mixture was further stirred still being cooled with ice water for 1 hour and at room temperature for another 1 hour. The reaction mixture was filtered through Celite, and concentrated under reduced pressure. After the remaining residue was extracted with EtOAc, the combined organic layers were washed with water and brine, dried with Na$_2$SO$_4$, and concentrated in vacuo. 410 mg of octanol (3.4 mmol, 59%, 2-octanol/1-octanol=71/29) was obtained after silica gel column chromatography.

The optical purity of the obtained 2-octanol was 94% ee (R configuration). Analytical method of optical purity (analyzed after benzoylation): Column; CHIRALPAK AD-H Example 29

Hydrosilylation of 1-octene (−)-5-(diphenylphosphino)-6-(2-methoxynaphthalen-1-yl)-4,7-dimethyl-1,3-dihydroisobenzofuran (26.7 mg, 0.0547 mmol, 92% ee) and allylpalladium chloride dimer (5.0 mg, 0.0137 mmol) were placed into a flask and the atmosphere in the flask was replaced with nitrogen. Toluene (1 mL) was added to dissolve them, and the solution was stirred at 30° C. for 30 minutes. After the bath was set at 40° C., toluene (3 mL) and 1-octene (3.1 g, 27.3 mmol) were added thereto, and the mixture was stirred for 30 minutes. Further, HSiCl$_3$ (4.44 g, 32.3 mmol) was added dropwise, and then the mixture was stirred for 24 hours. Analysis of the reaction mixture revealed that 2-trichlorosilyloctane/1-trichlorosilyloctane=76/24. HSiCl$_3$ and toluene was removed by using a Liebig condenser. 1.7 g of the silylated substance (6.9 mmol, 25%, 2-trichlorosilyloctane/1-trichlorosilyloctane=80/20) was obtained after distillation under reduced pressure.

Boiling point: 120-123° C./25 Torr

KF (2.0 g, 34.4 mmol) and KHCO$_3$ (6.9 g, 68.9 mmol) were placed into a round flask, suspended in MeOH-THF (1:1, 28 mL), and cooled with ice water. 1.4 g of the obtained silylated substance (5.8 mmol) was added dropwise, and then the mixture was stirred still being cooled with ice water for 1 hour and at room temperature for another 1 hour. Then, the mixture was cooled with ice water, and H$_2$O$_2$ (30% aqueous solution, 5.8 mL) was added dropwise still being kept in the bath overnight with stirring. The mixture was cooled with ice water, and Na$_2$S$_2$O$_3$5H$_2$O (7.2 g, 29.0 mmol) was added thereto. The mixture was further stirred still being cooled with ice water for 1 hour and at room temperature for another 1 hour. The reaction mixture was filtered through Celite, and concentrated in vacuo. After the remaining residue was extracted with EtOAc, the combined organic layers was washed with water and brine, dried with Na$_2$SO$_4$, and concentrated in vacuo. 460 mg of octanol (3.8 mmol, 61%, 2-octanol/1-octanol=71/29) was obtained after silica gel column chromatography.

The optical purity of the obtained 2-octanol was 85% ee (R configuration).

The above Ac and THF represent an acetyl group and tetrahydrofuran respectively.

What is claimed is:

1. A phosphorus compound defined by the following general formula (1):

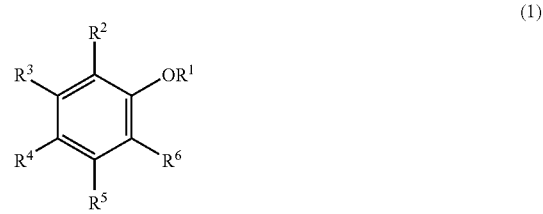

in the formula (1), $R^1$ denotes a hydrogen atom or a hydroxy protective group; $R^2$ denotes a group defined by the following formula ($R^2$-1) or ($R^2$-2); $R^3$, $R^4$, $R^5$, and $R^6$ may be the same or different and independently denote a hydrogen atom, an alkyl group, an alkoxy group, an acyloxy group, a halogen atom, a haloalkyl group, or a dialkylamino group; two among $R^3$, $R^4$, $R^5$, and $R^6$ may form an aromatic ring optionally having a substituent group, and two among $R^3$, $R^4$, $R^5$, and $R^6$ may form a methylene chain optionally having a substituent group or a (poly)methylenedioxy group optionally having a substituent group:

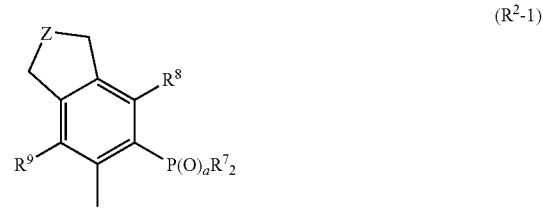

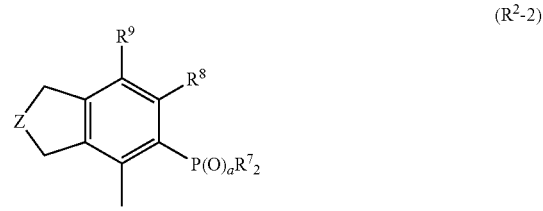

in the formula ($R^2$-1) and ($R^2$-2), $R^7$ denotes an alkyl group, a cycloalkyl group, an aryl group, an alkoxy group, or an aryloxy group; $R^8$ and $R^9$ independently denote a hydrogen atom, an alkyl group, or an aryl group; z denotes a divalent group selected from an oxygen atom, a sulfur atom, NR$^N$ and Si(R$^{Si}$)$_2$, R$^N$ denoting an alkyl, an aryl, an alkanesulfonyl, an arylsulfonyl, or an acyl group and R$^{Si}$ denoting an alkyl or an aryl group or Si(R$^{Si}$)$_2$ may form a ring; and (a) denotes an integer of 0 or 1.

2. The phosphorus compound according to claim 1, which is an axially asymmetric optically active substance.

3. The phosphorus compound according to claim 1, which is defined by the following general formula (3):

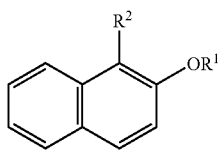

(3)

in the formula (3), $R^1$ denotes a hydrogen atom or a hydroxy protective group; $R^2$ denotes a group defined by the following formula ($R^2$-1) or ($R^2$-2):

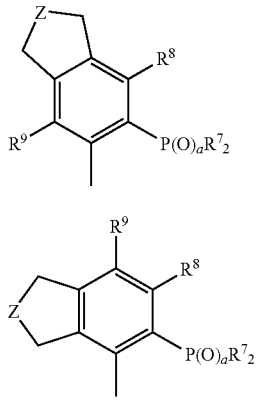

($R^2$-1)

($R^2$-2)

in the formula ($R^2$-1) and ($R^2$-2), $R^7$ denotes an alkyl group, a cycloalkyl group, an aryl group, an alkoxy group, or an aryloxy group; $R^8$ and $R^9$ independently denote a hydrogen atom, an alkyl group, or an aryl group; z denotes a divalent group selected from an oxygen atom, a sulfur atom, $NR^N$ and $Si(R^{Si})_2$, $R^N$ denoting an alkyl, an aryl, an alkanesulfonyl, an arylsulfonyl, or an acyl group and $R^{Si}$ denoting an alkyl or an aryl group or $Si(R^{Si})_2$ may form a ring; and (a) denotes an integer of 0 or 1.

4. The phosphorus compound according to claim 3, which is an axially asymmetric optically active substance.

5. A process for producing the phosphorus compound as claimed in claim 2, which comprises reacting a diyne compound defined by the following general formula (2-1) with an alkynyl phosphorus compound defined by the following general formula (3-1) by the use of a catalyst containing rhodium metal and an optically active bisphosphine:

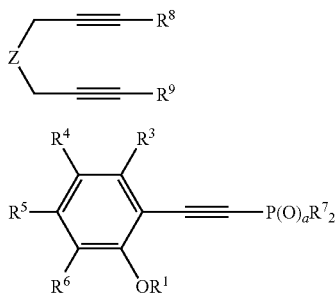

(2-1)

(3-1)

in the formula (2-1), $R^8$ and $R^9$ independently denote a hydrogen atom, an alkyl group, or an aryl group; z denotes a divalent group selected from an oxygen atom, a sulfur atom, $NR^N$ and $Si(R^{Si})_2$, $R^N$ denoting an alkyl, an aryl, an alkanesulfonyl, an arylsulfonyl, or an acyl group and $R^{Si}$ denoting an alkyl or an aryl group or $Si(R^{Si})_2$ may form a ring; and in the formula (3-1), $R^1$ denotes a hydrogen atom or a hydroxy protective group; $R^3$, $R^4$, $R^5$, and $R^6$ may be the same or different and independently denote a hydrogen atom, an alkyl group, an alkoxy group, an acyloxy group, a halogen atom, a haloalkyl group, or a dialkylamino group; two among $R^3$, $R^4$, $R^5$, and $R^6$ may form an aromatic ring optionally having a substituent group, and two among $R^3$, $R^4$, $R^5$, and $R^6$ may form a methylene chain optionally having a substituent group or a (poly)methylenedioxy group optionally having a substituent group; $R^7$ denotes an alkyl group, a cycloalkyl group, an aryl group, an alkoxy group, or an aryloxy group; and a denotes an integer of 0 or 1.

6. A process for producing the phosphorus compound as claimed in claim 2, which comprises reacting a diyne compound defined by the following general formula (2-2) with an alkynyl phosphorus compound defined by the following general formula (3-2) by the use of a catalyst containing rhodium metal and an optically active bisphosphine:

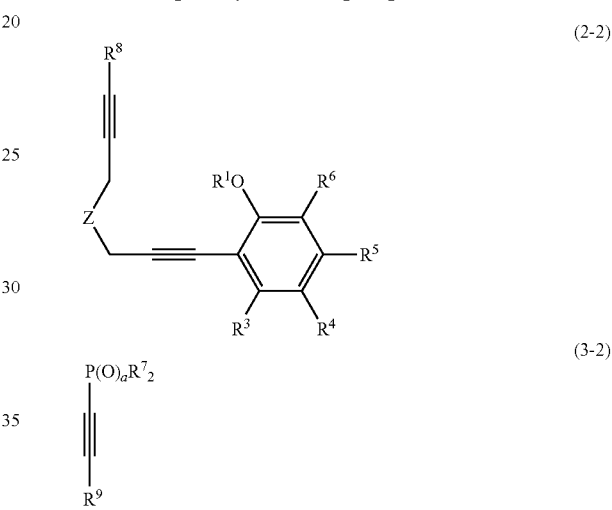

(2-2)

(3-2)

in the formula (2-2), $R^1$ denotes a hydrogen atom or a hydroxy protective group; $R^3$, $R^4$, $R^5$, and $R^6$ may be the same or different and independently denote a hydrogen atom, an alkyl group, an alkoxy group, an acyloxy group, a halogen atom, a haloalkyl group, or a dialkylamino group; two among $R^3$, $R^4$, $R^5$, and $R^6$ may form an aromatic ring optionally having a substituent group, and two among $R^3$, $R^4$, $R^5$, and $R^6$ may form a methylene chain optionally having a substituent group or a (poly)methylenedioxy group optionally having a substituent group; $R^8$ denotes a hydrogen atom, an alkyl group, or an aryl group; z denotes a divalent group selected from an oxygen atom, a sulfur atom, $NR^N$ and $Si(R^{Si})_2$, $R^N$ denoting an alkyl, an aryl, an alkanesulfonyl, an arylsulfonyl, or an acyl group and $R^{Si}$ denoting an alkyl or an aryl group or $Si(R^{Si})_2$ may form a ring; and in the formula (3-2), $R^7$ denotes an alkyl group, a cycloalkyl group, an aryl group, an alkoxy group, or an aryloxy group; $R^9$ denotes a hydrogen atom, an alkyl group, or an aryl group; and a denotes an integer of 0 or 1.

7. The process according to claim 5, wherein the catalyst containing rhodium metal and an optically active bisphosphine is a compound defined by the following general formula (4):

$$[Rh(L)_m(Y)_n]X \qquad (4)$$

in the formula (4), L denotes an optically active bisphosphine defined by the following formula (5); Y denotes a nonconjugated diene compound; X denotes a counter anion; m denotes an integer of 1 or 2; n denotes an integer of 0 or 1; however, in the case where m=1, n=0 or n=1; and in the case where m=2, n=0:

  (5)

in the formula (5), $R^{10}$, $R^{11}$, $R^{12}$, and $R^{13}$ independently denote an aryl group optionally having a substituent group or a cycloalkyl group optionally having a substituent group; $R^{10}$ in combination with $R^{11}$ and/or $R^{12}$ in combination with $R^{13}$ may form a ring; and Q denotes a divalent arylene group optionally having a substituent group or a ferrocenediyl group.

8. The process according to claim 7, wherein the catalyst containing rhodium metal and an optically active bisphosphine is used immediately after preparation.

9. The process according to claim 7, wherein an olefin ligand is eliminated using hydrogen gas in preparing the catalyst containing rhodium metal and an optically active bisphosphine.

10. The process according to claim 6, wherein the catalyst containing rhodium metal and an optically active bisphosphine is a compound defined by the following general formula (4):

  (4)

in the formula (4), L denotes an optically active bisphosphine defined by the following formula (5); Y denotes a nonconjugated diene compound; X denotes a counter anion; m denotes an integer of 1 or 2; n denotes an integer of 0 or 1; however, in the case where m=1, n=0 or n=1; and in the case where m=2, n=0:

  (5)

in the formula (5), $R^{10}$, $R^{11}$, $R^{12}$, and $R^{13}$ independently denote an aryl group optionally having a substituent group or a cycloalkyl group optionally having a substituent group; $R^{10}$ in combination with $R^{11}$ and/or $R^{12}$, in combination with $R^{13}$ may form a ring; and Q denotes a divalent arylene group optionally having a substituent group or a ferrocenediyl group.

11. The process according to claim 8, wherein an olefin ligand is eliminated using hydrogen gas in preparing the catalyst containing rhodium metal and an optically active bisphosphine.

* * * * *